(12) United States Patent
Kameda et al.

(10) Patent No.: US 9,629,754 B2
(45) Date of Patent: Apr. 25, 2017

(54) MANUFACTURING METHOD AND MANUFACTURING APPARATUS FOR A COMPOSITE SHEET ASSOCIATED WITH AN ABSORBENT ARTICLE

(71) Applicant: Uni-Charm Corporation, Ehime (JP)

(72) Inventors: Noritomo Kameda, Kanonji (JP); Shinichi Ishikawa, Kanoji (JP)

(73) Assignee: UNICHARM CORPORATION, Ehime (JP)

( * ) Notice: Subject to any disclaimer, the term of this patent is extended or adjusted under 35 U.S.C. 154(b) by 945 days.

(21) Appl. No.: 13/940,616

(22) Filed: Jul. 12, 2013

(65) Prior Publication Data

US 2015/0013916 A1 Jan. 15, 2015
US 2017/0000653 A9 Jan. 5, 2017

Related U.S. Application Data

(62) Division of application No. 13/322,707, filed as application No. PCT/JP2010/059133 on May 28, 2010, now Pat. No. 8,591,682.

(30) Foreign Application Priority Data

Jun. 5, 2009 (JP) .................................. 2009-136523

(51) Int. Cl.
*A61F 13/00* (2006.01)
*A61F 13/15* (2006.01)

(52) U.S. Cl.
CPC .............................. *A61F 13/15609* (2013.01)

(58) Field of Classification Search
CPC .... A61F 13/00; A61F 13/15609; A61F 13/15; A61F 13/15577
See application file for complete search history.

(56) References Cited

U.S. PATENT DOCUMENTS 4,371,417 A * 2/1983 Frick ................. A61F 13/15593
112/470.32
5,779,689 A 7/1998 Pfeifer et al.
(Continued)

FOREIGN PATENT DOCUMENTS

JP 6-502091 A 3/1994
JP 08-280740 A 10/1996
(Continued)

OTHER PUBLICATIONS

Corresponding U.S. Appl. No. 13/322,707 Notice of Allowance dated Jul. 23, 2013.
(Continued)

*Primary Examiner* — Michael N Orlando
*Assistant Examiner* — Matthew Hoover
(74) *Attorney, Agent, or Firm* — Hauptman Ham, LLP

(57) ABSTRACT

A manufacturing apparatus for a composite sheet associated with an absorbent article including: a conveying mechanism that conveys continuously the continuous body of the sheet; and a guiding member that transports the continuous body of the elastic member, and that bonds the continuous body of the elastic member with the continuous body of the sheet, wherein the guiding member includes a drive roller that, while being contact with the continuous body of the elastic member, is driven and rotated along a transporting direction of the continuous body of the elastic member, and by changing a rotation speed of the drive roller, a stretching ratio of the continuous body of the elastic member is adjusted.

11 Claims, 11 Drawing Sheets

(56) References Cited

U.S. PATENT DOCUMENTS

| | | | |
|---|---|---|---|
| 6,284,081 B1* | 9/2001 | Vogt | A61F 13/15609 156/161 |
| 6,589,149 B1 | 7/2003 | VanEperen et al. | |
| 8,591,682 B2* | 11/2013 | Kameda | A61F 13/15601 156/160 |
| 2003/0120245 A1* | 6/2003 | Franklin | A61F 13/15593 604/385.27 |
| 2010/0078127 A1* | 4/2010 | Yamamoto | A61F 13/15609 156/306.3 |
| 2012/0118485 A1* | 5/2012 | Kameda | A61F 13/15609 156/164 |

FOREIGN PATENT DOCUMENTS

| | | |
|---|---|---|
| JP | 09-000564 A | 1/1997 |
| JP | 10-179635 A | 7/1998 |
| JP | 11-322147 A | 11/1999 |
| JP | 2001-346825 A | 12/2001 |
| JP | 2004-505725 A | 2/2004 |
| JP | 2010-094240 A | 4/2010 |
| WO | 01/45611 A1 | 6/2001 |
| WO | 2010-044324 A1 | 4/2010 |

OTHER PUBLICATIONS

International Search Report for PCT/JP2010/059133 mailed Aug. 31, 2010.
Corresponding Chinese Application No. 201080024530.X Office Action dated May 6, 2013.

* cited by examiner

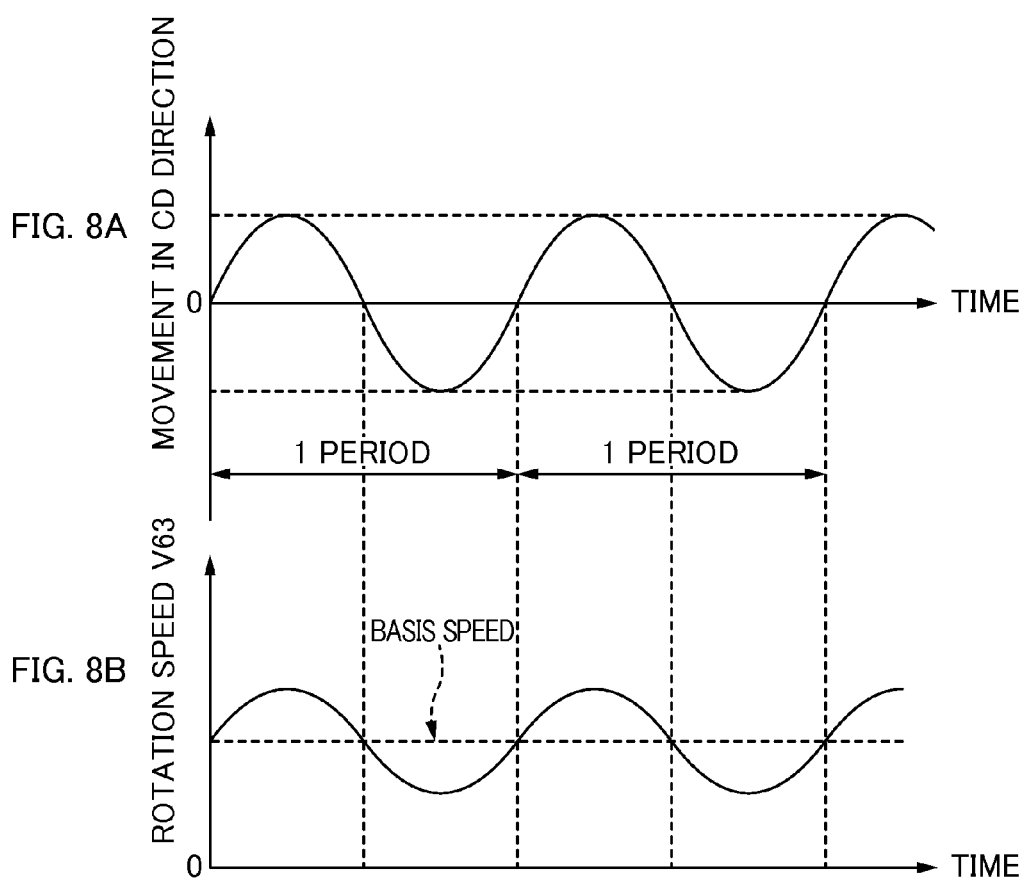

MANUFACTURING METHOD AND MANUFACTURING APPARATUS FOR A COMPOSITE SHEET ASSOCIATED WITH AN ABSORBENT ARTICLE

RELATED APPLICATIONS

The present application is a Divisional of U.S. patent application Ser. No. 13/322,707, filed Feb. 1, 2012, and is based on International Application Number PCT/JP2010/059133 filed May 28, 2010, and claims priority from Japanese Application Number 2009-136523, filed Jun. 5, 2009, the disclosures of which is hereby incorporated by reference herein in its entirety

TECHNICAL FIELD

The invention relates to manufacturing method and manufacturing apparatus for a composite sheet associated with an absorbent article.

BACKGROUND ART

As an example of an absorbent article to absorb exudates, a traditional disposable diaper, etc are well-known. In the manufacturing line thereof, the continuous body of a sheet is conveyed continuously in a conveying direction, and the process is performed in which a continuous body of an elastic member such as rubber thread is bonded with the continuous body continuously in a curved pattern such as an approximate sine curve, etc.

In patent literature 1, a method for the bonding is disclosed in which, as shown in FIG. 1, by using a guide head 220 that moves back and forth in a direction intersecting the conveying direction of the continuous body 200 of a sheet, the guide head 220 moves the continuous body 201 of an elastic member back and forth and transport it to the continuous body 200 of the sheet, thereby bonding the continuous body 201 therewith in a desired curved pattern.

Further, the patent literature 1 discloses the technique that in the bonding the stretching ratio of the continuous body 201 is changed corresponding to the curved pattern periodically, thereby providing the continuous body 201 with an elastic force of a corresponding magnitude to each section in the curved pattern. That is, in a position upstream than the guide head 220, a pair of upper and lower variable-speed rolls 230a and 230b are installed independently of the guide head 220. While the continuous body 201 of the elastic member is sandwiched between the a pair of upper and lower variable-speed rolls 230a and 230b, the rotation speed of these variable-speed rolls 230a and 230b is adjusted. Thereby, while changing the stretching ratio of the continuous body 201, the continuous body 201 is fed into the guide head 220.

CITATION LIST

Patent Literature

[PTL 1] Japanese Patent Application Laid-open Publication No. 2001-346825

SUMMARY OF THE INVENTION

Technical Problem

However, the variable-speed rolls 230a and 230b are installed a distance D from the guide head 220. Therefore, the stretching ratio is provided to each section in the curved pattern with a delay corresponding to the distance D. As a result, it is difficult to provide the stretching ratio of a desired corresponding magnitude to each section in the curved pattern.

Further, even if the rotation speed of the variable-speed rolls 230a and 230b changes in order to change the stretching ratio, the change of the stretching ratio is smoothed out while the continuous body 201 is moving in the path D from the variable-speed rolls 230a and 230b to the guide head 220. As a result, it is difficult to set an obviously different stretching ratio to each section in the curved pattern.

The invention has been made in view of the above problems, and an advantage thereof is to provide a manufacturing method and a manufacturing apparatus for a composite sheet associated with an absorbent article in which, when a continuous body of an elastic member bonds with a continuous body of a sheet in a predetermined curved pattern, it is easier to provide a stretching ratio having a corresponding magnitude to each section of the curved pattern and it is easier to set a practically different stretching ratio to each section in the curved pattern.

Solution to Problem

An aspect of the invention to achieve the above advantage is a manufacturing method for a composite sheet associated with an absorbent article, in which a continuous body of an elastic member is in a stretched state and is bonded with a continuous body of a sheet, including:

conveying the continuous body of the sheet continuously in a conveying direction; and bonding the continuous body of the elastic member with the continuous body of the sheet while a position on the continuous body of the sheet at which the continuous body of the elastic member bonds with the continuous body of the sheet is changing continuously in the intersecting direction by transporting the continuous body of the elastic member towards the continuous body of the sheet with a guiding member, the guiding member moving back and forth in an intersecting direction that intersects the conveying direction, the continuous body of the sheet being traveling in the conveying direction, wherein the guiding member includes a drive roller that, while being contact with the continuous body of the elastic member, is driven and rotated along a transporting direction of the continuous body of the elastic member, and by changing a rotation speed of the drive roller, a stretching ratio of the continuous body of the elastic member is adjusted.

Further,

A manufacturing apparatus for a composite sheet associated with an absorbent article, in which a continuous body of an elastic member is in a stretched state and is bonded with a continuous body of a sheet, including:

a conveying mechanism that conveys continuously the continuous body of the sheet in a conveying direction; and a guiding member that transports the continuous body of the elastic member towards the continuous body of the sheet while moving back and forth the continuous body of the elastic member in an intersecting direction that intersects the conveying direction, the continuous body of the sheet being traveling in the conveying direction, and that bonds the continuous body of the elastic member with the continuous body of the sheet while a position on the continuous body of the sheet at which the continuous body of the elastic member bonds with the continuous body of the sheet is continuously changing in the intersecting direction by the transporting, wherein the guiding member includes a drive roller that, while being contact with the continuous body of the elastic member, is driven and rotated along a transporting direction of the continuous body of the elastic member, and by changing a rotation speed of the drive roller, a stretching ratio of the continuous body of the elastic member is adjusted.

Effects of the Invention

According to the invention, when bonding the continuous body of a sheet and the continuous body of an elastic member in a predetermined curved pattern, it is easier to provide a stretching ratio having a corresponding magnitude to each section of the curved pattern, and it is easier to set a practically different stretching ratio to each section in the curved pattern.

BRIEF DESCRIPTION OF THE DRAWINGS

FIG. 8A is a timing chart of an oscillating motion of the oscillating arm 61, and FIG. 8B is a timing chart of the rotation speed V63 of the oscillating-end roll 63.

MODE FOR CARRYING OUT THE INVENTION

Figure 1:
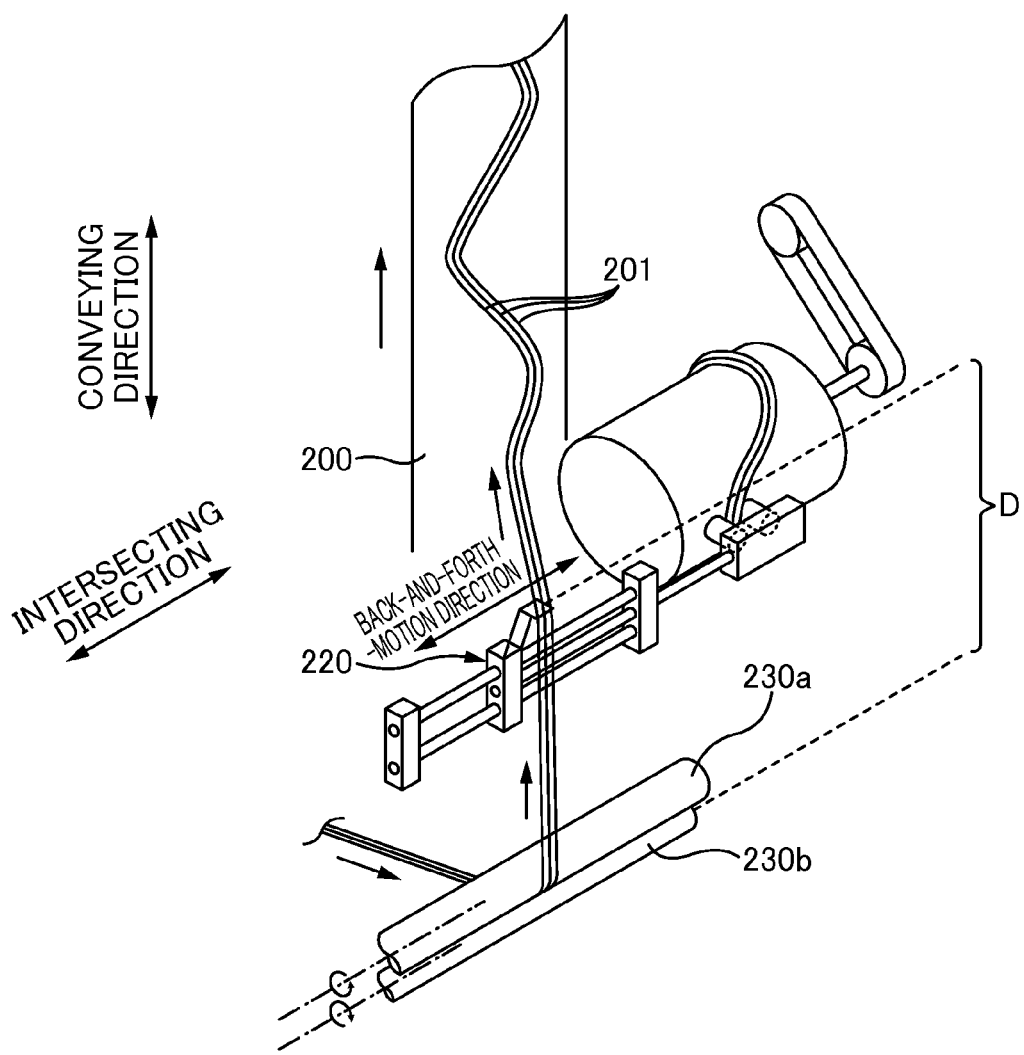
FIG. 1 is a perspective view showing a conventional method for bonding the continuous body 201 of an elastic member with the continuous body 200 of a sheet in a curved pattern.

At least the following matters will be made clear by the description in the present specification and the accompanying drawings.

A manufacturing method for a composite sheet associated with an absorbent article, in which a continuous body of an elastic member is in a stretched state and is bonded with a continuous body of a sheet, including conveying the continuous body of the sheet continuously in a conveying direction; and bonding the continuous body of the elastic member with the continuous body of the sheet while a position on the continuous body of the sheet at which the continuous body of the elastic member bonds with the continuous body of the sheet is changing continuously in the intersecting direction by transporting the continuous body of the elastic member towards the continuous body of the sheet with a guiding member, the guiding member moving back and forth in an intersecting direction that intersects the conveying direction, the continuous body of the sheet being traveling in the conveying direction, wherein the guiding member includes a drive roller that, while being contact with the continuous body of the elastic member, is driven and rotated along a transporting direction of the continuous body of the elastic member, and by changing a rotation speed of the drive roller, a stretching ratio of the continuous body of the elastic member is adjusted.

With such a manufacturing method for a composite sheet associated with an absorbent article, the drive roller performs concurrently both of forming the curved pattern of the continuous body of the elastic member and adjusting the stretching ratio of the continuous body of the elastic member. This makes it easier to provide each section of the curved pattern with a desired stretching ratio corresponding to the section.

Further, as mentioned above, the drive roller functions as a device for forming the curved pattern and a device for providing the stretching ratio. Therefore, the length of the path between the device for forming the curved pattern and the device for providing the stretching ratio is zero. This can prevent the stretching ratio from being smoothed out on the course of the path. As a result, it is easier to set a practically different stretching ratio to each section in the curved pattern.

In such a manufacturing method for a composite sheet associated with an absorbent article, desirably the drive roller is a member that is located farthest downstream in the transporting direction, among members that come into contact with the continuous body of the elastic member on a path prior to the bonding of the continuous body of the elastic member with the continuous body of the sheet.

With such a manufacturing method for a composite sheet associated with an absorbent article, the drive roller is a member that is located farthest downstream among members which can come into contact with the continuous body of the elastic member prior to the bonding. Therefore, the stretching ratio of the continuous body of the elastic member can change definitely by changing the rotation speed of the drive roller.

In such a manufacturing method for a composite sheet associated with an absorbent article, desirably a length of a path of the continuous body of the elastic member after leaving the drive roller up to the bonding with the continuous body of the sheet is from 30 to 80 mm.

With such a manufacturing method for a composite sheet associated with an absorbent article, the path length is 30 to 80 mm. This can reduce the degree of smoothing of the stretching ratio in the path length. As a result, it is easier to set a practically different stretching ratio to each section in the curved pattern.

In such a manufacturing method for a composite sheet associated with an absorbent article, desirably the guiding member includes an oscillating arm that oscillates about a predetermined axis in the intersecting direction, the drive roller is disposed on the oscillating end of the oscillating arm, a second roller is disposed on the oscillating arm at a position closer to the axis than the drive roller is, the continuous body of the elastic member fed into the second roller is transported to the drive roller, the drive roller is driven and rotated by a drive mechanism, and the drive mechanism includes a drive pulley that is disposed so as to rotate about a same axis as the drive roller in an integrated manner with the drive roller, a relay pulley that is arranged on the oscillating arm at a position closer to the axis than the drive pulley is, an endless belt that is wrapped around the drive pulley and the relay pulley, and a second drive mechanism that drives and rotates the relay pulley.

With such a manufacturing method for a composite sheet associated with an absorbent article, it is not necessary to install a power source, such as a motor etc, on the oscillating end of the oscillating arm. This can reduce the moment of inertia of the oscillating arm about the axis. Therefore, driving torque for the oscillating motion can be reduced, and the response of the oscillating motion of the oscillating arm becomes better.

In such a manufacturing method for a composite sheet associated with an absorbent article, desirably the second roller is fixed to the relay pulley on a same axis as the relay pulley so as to rotate in an integrated manner with the relay pulley, a driving torque is transmitted to the second roller from the endless belt through the relay pulley in order to drive and rotate the second roller, and, the driving torque rotates the second roller at a same peripheral speed as the drive roller.

With such a manufacturing method for a composite sheet associated with an absorbent article, in changing the peripheral speed of the drive roller, the peripheral speed of the second roller is also changed in synchronization therewith. Therefore, the transportation of the continuous body of the elastic member is controlled by at least these two rollers. This can effectively prevent the drive roller from slipping relative to the continuous body of the elastic member when changing the peripheral speed of the drive roller. As a result, the change of the stretching ratio can respond better to the change of the rotation speed, that is, the peripheral speed.

In such a manufacturing method for a composite sheet associated with an absorbent article, desirably the second drive mechanism includes a drive shaft that is driven and rotated, a second relay pulley that is disposed so as to rotate about a same axis as the relay pulley in an integrated manner with the relay pulley, and a second endless belt that is wrapped around the drive shaft and the second relay pulley, and in a path of the second endless belt, a section from the drive shaft to the second relay pulley is parallel to a rotation centerline of the axis.

With such a manufacturing method for a composite sheet associated with an absorbent article, the second relay pulley is located on the oscillating arm at a position closer to the axis. And, the section in the path of the second endless belt is parallel to the rotation centerline of the axis. This can effectively prevent torsion of the endless belt caused by the oscillating motion of the oscillating arm.

In such a manufacturing method for a composite sheet associated with an absorbent article, desirably the guiding member includes an oscillating arm that oscillates about a predetermined axis in the intersecting direction, the drive roller is disposed on an oscillating end of the oscillating arm, a second roller is disposed on the oscillating arm at a position closer to the axis than the drive roller is, the continuous body of the elastic member fed into the second roller is transported to the drive roller, and the second roller is driven and rotated so as to rotate at a same peripheral speed as the drive roller.

With such a manufacturing method for a composite sheet associated with an absorbent article, in changing the peripheral speed of the drive roller, the peripheral speed of the second roller is also changed in synchronization therewith. Therefore, the transportation of the continuous body of the elastic member is controlled by at least these two rollers. This can effectively prevent the drive roller from slipping relative to the continuous body of the elastic member when changing the peripheral speed of the drive roller. As a result, the change of the stretching ratio can respond better to the change of the rotation speed, that is, the peripheral speed.

In such a manufacturing method for a composite sheet associated with an absorbent article, desirably the continuous body of the elastic member is wrapped around an outer peripheral face of the drive roller with a wrap angle of 90 degree or more.

With such a manufacturing method for a composite sheet associated with an absorbent article, setting the wrap angle as mentioned above can increase the friction between the drive roller and the continuous body of the elastic member. Therefore, the friction can improve the transmission of the rotation of the drive roller to the continuous body of the elastic member. As a result, changing the rotation speed of the drive roller makes it possible to adjust the stretching ratio of the elastic member with high response rate.

In such a manufacturing method for a composite sheet associated with an absorbent article, desirably the guiding member is provided with a rotatable pressing roll opposite to an outer peripheral face of the drive roller, and the pressing roll presses the continuous body of the elastic member against the outer peripheral face of the drive roller, the continuous body being contact with the outer peripheral face.

With such a manufacturing method for a composite sheet associated with an absorbent article, the continuous body of the elastic member is sandwiched and held between the drive roller and the pressing roll. This can improve the transmission of the rotation of the drive roller to the continuous body of the elastic member. As a result, changing the rotation speed of the drive roller makes it possible to adjust the stretching ratio of the elastic member with high response rate.

In such a manufacturing method for a composite sheet associated with an absorbent article, desirably the continuous body of the elastic member is a band member having a width.

With such a manufacturing method for a composite sheet associated with an absorbent article, it is possible to effectively achieve the foregoing operation and effect. The detail is as follows. The band member is wider than a thread member, and therefore an elastic force can change sensitively to the change of the stretching amount. That is, a small change in the stretching amount will cause a great change in the elastic force of the band member. Therefore, when a desired elastic force is provided to the band member, a fine control of the stretching amount is needed. In this point, as mentioned above, the invention can effectively prevent the stretching ratio from being smoothing out, and a finer control of the stretching amount can be achieved. Therefore, the invention becomes more effective especially if the continuous body of the elastic member is a band member.

In such a manufacturing method for a composite sheet associated with an absorbent article, desirably the rotation speed of the drive roller is changed in conjunction with a back-and-forth motion of the guiding member.

With such a manufacturing method for a composite sheet associated with an absorbent article, by changing the rotation speed of the drive roller, a desired stretching ratio corresponding to each section of the curved pattern can be provided definitely to the section.

In such a manufacturing method for a composite sheet associated with an absorbent article, desirably within a time period including a turning point for the back-and-forth motion, prior to passing the turning point, the rotation speed of the drive roller is less than a predetermined reference velocity, and after passing the turning point, the rotation speed is greater than the reference velocity.

With such a manufacturing method for a composite sheet associated with an absorbent article, it is possible to prevent the stretching ratio of the continuous body of the elastic member immediately after the turning point of the back-and-forth motion from becoming higher than the stretching ratio immediately before the turning point. This enables the stretching ratio to be uniform.

In such a manufacturing method for a composite sheet associated with an absorbent article, desirably the rotation speed of the drive roller is periodically changed based on a predetermined speed pattern, a period of a back-and-forth motion of the drive roller is the same as a period of the speed pattern, the speed pattern is delayed by a predetermined phase from the back-and-forth motion.

With such a manufacturing method for a composite sheet associated with an absorbent article, to each section of the continuous body of the elastic member on the curved pattern, a desired stretching ratio precisely corresponding thereto can be provided. This is because while the continuous body of the elastic member moves back and forth with a slight delay from the back-and-forth motion of the drive roller and is bonded with the continuous body of the sheet, the change of the rotation speed of the drive roller is transmitted relatively instantly to the bonding position of the continuous body of the sheet and the continuous body of the elastic member.

Further,

A manufacturing apparatus for a composite sheet associated with an absorbent article, in which a continuous body of an elastic member is in a stretched state and is bonded with a continuous body of a sheet, including:

a conveying mechanism that conveys continuously the continuous body of the sheet in a conveying direction; and a guiding member that transports the continuous body of the elastic member towards the continuous body of the sheet while moving back and forth the continuous body of the elastic member in an intersecting direction that intersects the conveying direction, the continuous body of the sheet being traveling in the conveying direction, and that bonds the continuous body of the elastic member with the continuous body of the sheet while a position on the continuous body of the sheet at which the continuous body of the elastic member bonds with the continuous body of the sheet is continuously changing in the intersecting direction by the transporting, wherein the guiding member includes a drive roller that, while being contact with the continuous body of the elastic member, is driven and rotated along a transporting direction of the continuous body of the elastic member, and by changing a rotation speed of the drive roller, a stretching ratio of the continuous body of the elastic member is adjusted.

With such a manufacturing apparatus for a composite sheet associated with an absorbent article, the drive roller performs concurrently both of forming the curved pattern of the continuous body of the elastic member and adjusting the stretching ratio of the continuous body of the elastic member. This makes it easier to provide each section of the curved pattern with a desired stretching ratio corresponding to the section.

Further, as mentioned above, the drive roller functions as a device for forming the curved pattern and a device for providing the stretching ratio. Therefore, the length of the path between the device for forming the curved pattern and the device for providing the stretching ratio is zero. This can prevent the stretching ratio from being smoothed out on the course of the path. As a result, it is easier to set a practically different stretching ratio to each section in the curved pattern.

Present Embodiment

A manufacturing method and manufacturing apparatus 40 for a composite sheet according to the present embodiment are applied to, for example, a manufacturing line for disposable diapers 1 (corresponding to absorbent articles).

<<<Diaper 1>>>

Figure 2A:
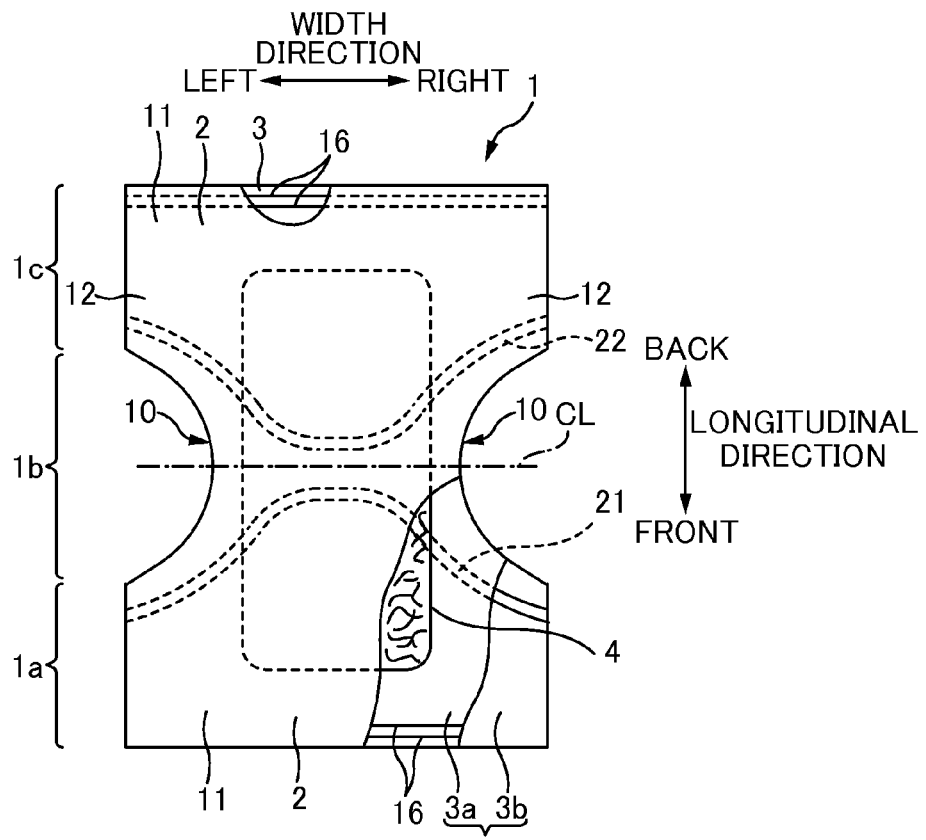
FIG. 2A is a partially-exploded plan view of a diaper 1.
Figure 2B:
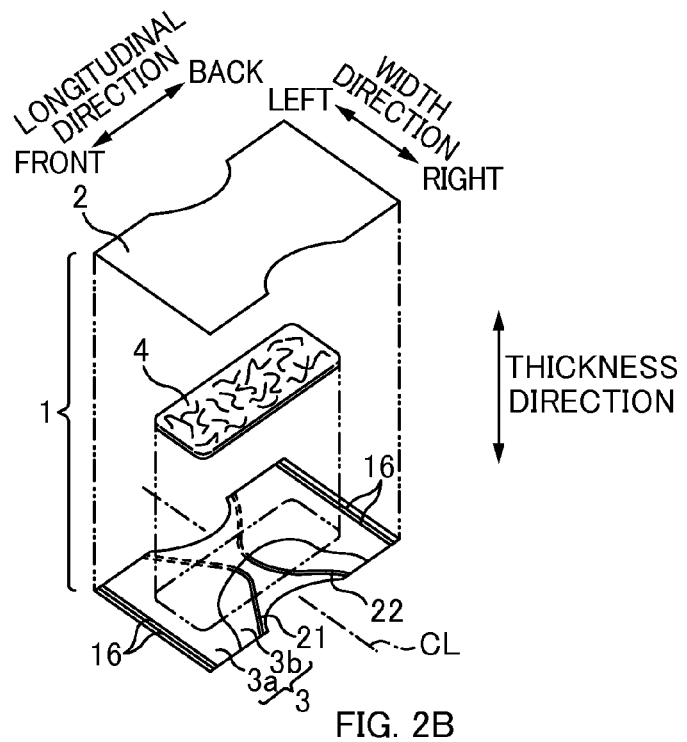
FIG. 2B is an exploded perspective view of the diaper 1.

FIG. 2A is a partially-exploded plan view of the diaper 1, and FIG. 2B is an exploded perspective view of the diaper 1. Both figures show the exploded views of the pull-on diaper 1 in which a front waistband section 1a and a back waistband section 1c are separated from each other on the sides of the diaper.

The diaper 1 has a longitudinal direction, a width direction, and a thickness direction which are perpendicular to one another. The front waistband section 1a, a crotch section 1b, and the back waistband section 1c are defined along the longitudinal direction of the diaper 1. The diaper 1 includes, in the thickness direction, a liquid-permeable surface sheet 2, a liquid-impermeable back face sheet 3, and a liquid-absorbent absorbent body 4; the absorbent body 4 is disposed between these sheets 2 and 3. The surface sheet 2 and the back face sheet 3 overlap in a section extending outwardly beyond the absorbent body 4, which are bonded with hot melt adhesive etc. Therefore, longitudinal end flaps 11 are formed on the front and back ends in the longitudinal direction, and side end flaps 12 are formed on the left and right sides in the width direction. On the side end flaps 12, leg opening sections 10 are formed in the crotch section 1b and are curved inwardly in the width direction. The diaper 1 is substantially in hourglass shape as a whole.

In the surface sheet 2, liquid permeable plastic film, nonwoven fabric, etc are employed, for example.

The back face sheet 3 includes an inner sheet 3a and an outer sheet 3b; the inner sheet 3a faces the surface sheet 2 and the outer sheet 3b faces that inner sheet 3a. These sheets 3a and 3b are the same in shape and size, and are bonded by adhesion or welding. For the inner sheet 3a, liquid-impermeable plastic film, nonwoven fabric, etc are employed, and for the outer sheet 3b, air-permeable nonwoven fabric, etc are employed.

On each of the longitudinal end flaps 11 in front and back waistband sections 1a and 1c, waist elastic members 16 are disposed between the surface sheet 2 and the back face sheet 3, and are bonded therewith in the stretched condition.

Further, in the crotch section 1b and the vicinity thereof, a front elastic ribbon 21 and a back elastic ribbon 22 are disposed across the diaper 1 along the width direction. For these elastic ribbons 21 and 22, nonwoven fabric, band-like rubber, etc which have stretchability are employed, for example. Each of these elastic ribbons 21 and 22 extends in the width direction in a predetermined curved pattern which forms a curve towards the centerline CL which divides the diaper 1 substantially in halves in the longitudinal direction. The elastic ribbons 21 and 22 are disposed between the inner sheet 3a and the outer sheet 3b, which the back face sheet 3 consists of. The elastic ribbons 21 and 22 are bonded with an inner surface of, for example, the outer sheet 3b in the stretched condition. The front and back elastic ribbons 21 and 22 provides together a stretchability on the leg opening sections 10.

In this example, sine curve is provided as an example of a curved pattern of these elastic ribbons 21 and 22. However, the curved pattern can be changed properly so that the leg opening sections 10 effectively fit a wearer of the diaper along the legs of the wearer.

Figure 3:
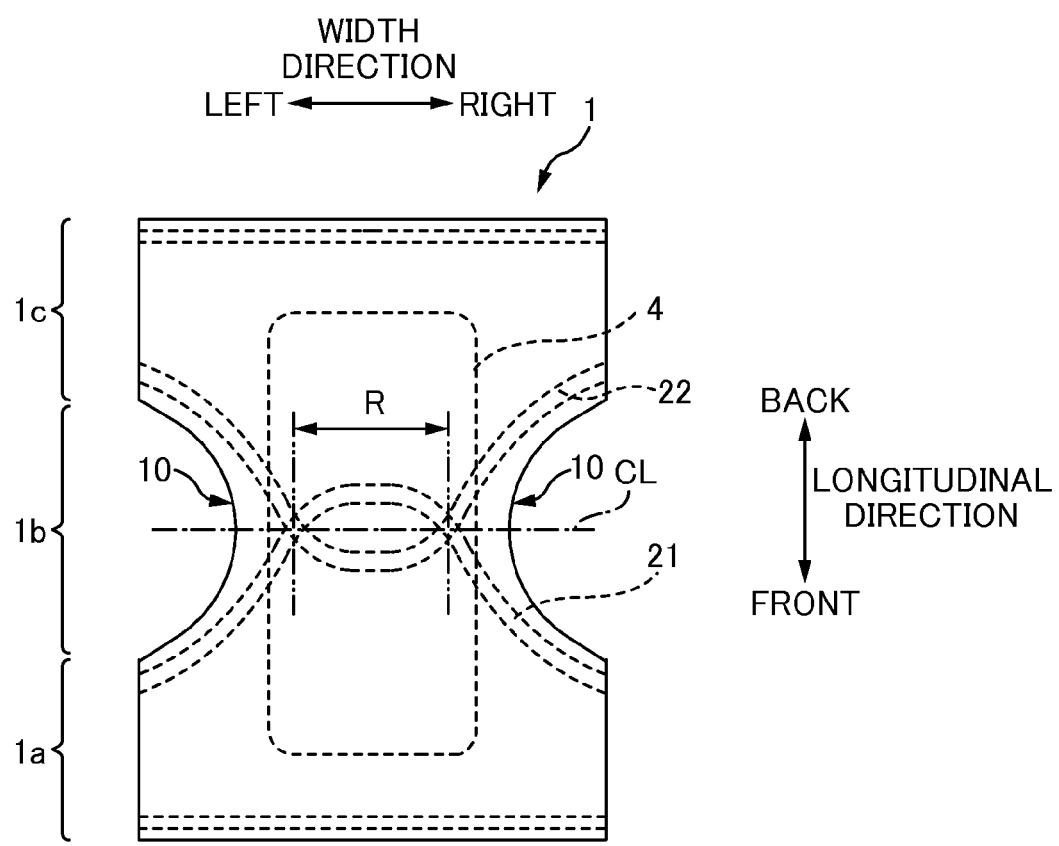
FIG. 3 is a plan view of the diaper 1 on which elastic ribbons 21 and 22 are arranged so as to intersect each other at a turning section of each curved pattern.

Further, in order for the leg opening sections 10 to fit the user's body throughout substantially total length of the section, as shown in FIG. 3, it is possible to arrange the elastic ribbons 21 and 22 so that the elastic ribbons intersect in turning sections of the curved pattern. Further, in order to reduce stretchability in the area R where the elastic ribbons intersect, it is possible to separate portions of the elastic ribbons 21 and 22 within the area R. In this regard, the reason for reducing the stretchability in the area R is that if the stretchability affects on any section over the absorbent body 4, the absorbent body 4 creases and the absorbent ability thereof may deteriorate.

<<<Manufacturing Method and Manufacturing Apparatus 40 for Composite Sheet>>>

The foregoing diaper 1 is finished by bonding various components with a base material of the diaper 1, the base material continuously flowing in a manufacturing line. A process in the manufacturing line is performed by a manufacturing method and a manufacturing apparatus 40 for a composite sheet according to the present embodiment. That is, in this embodiment, the apparatus and the method are applied to a process in which a continuous body 121 of an elastic ribbon (corresponding to "continuous body of the elastic member") is bonded with a continuous body 103b of a sheet in the foregoing curved pattern; the continuous body 103b is to be the outer sheet 3b of the foregoing back face sheet 3 and the continuous body 121 is to be the foregoing front elastic ribbon 21. In the following description, the continuous body 103b of sheet is merely referred to as "sheet 103b", and the continuous body 121 of the elastic ribbon is merely referred to as "elastic ribbon 121". Also, a description of the back elastic ribbon 22 is omitted because obviously the ribbon 22 can be bonded in the same method.

Figure 4A:
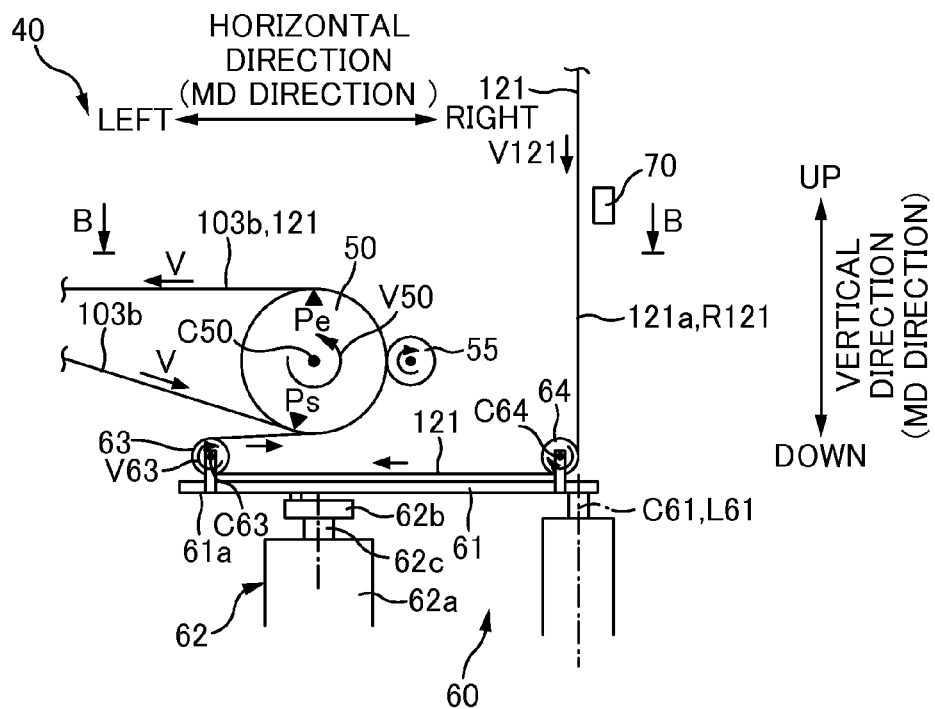
FIG. 4A is a side view of a manufacturing apparatus for a composite sheet 40 according to the present embodiment.
Figure 4B:
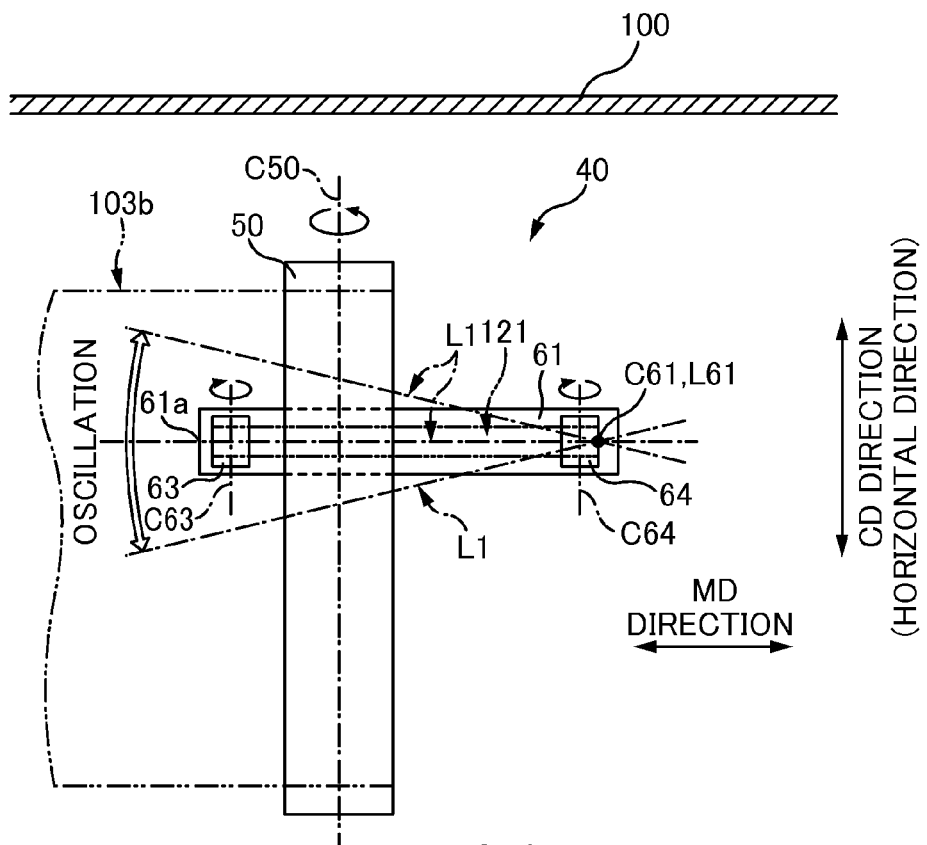
FIG. 4B is a view taken along line B-B in FIG. 4A.

FIG. 4A is a side view of the manufacturing apparatus 40 in the foregoing process, and FIG. 4B is a view taken along line B-B in FIG. 4A. In the following description, the width direction of the manufacturing apparatus 40 is referred to as a CD direction, and a direction perpendicular to the CD direction is referred to as an MD direction. That is, the MD direction means any direction in a plane which is perpendicular to the CD direction. Further, the MD direction is defined as two directions perpendicular to each other as shown in FIG. 4A: the up-and-down direction (vertical direction) and the left-to-right direction (horizontal direction). In this regard, the CD direction is in the horizontal direction and is perpendicular to the left-to-right direction, which is in the horizontal direction in similarity to the CD direction.

The manufacturing apparatus 40 includes: (1) a conveying roller 50 (corresponding to conveying mechanism); (2) a guiding member 60; and (3) an applying device 70. The conveying roller 50 conveys the sheet 103b in the MD direction (corresponding to conveying direction) by rotating with the sheet 103b being wrapped around it with a predetermined wrapping angle. The guiding member 60 continuously feeds the stretched elastic ribbon 121 and bonds the ribbon 121 with a section of the sheet 103b which is wrapped around and is in contact with an outer peripheral face of the conveying roller 50. The applying device 70 applies hot melt adhesive to the elastic ribbon 121 in order to bond the elastic ribbon 121 and the sheet 103b.

The guiding member 60 transports the elastic ribbon 121 towards the sheet 103b in a transporting direction while moving the elastic ribbon 121 back and forth in the CD direction (corresponding to intersecting direction). The transporting direction is a direction perpendicular to the direction in which the elastic ribbon 121 is moving back and forth. Therefore, a position at which the elastic ribbon 121 is bonded with the sheet 103b is changing gradually continuously in the CD direction, and the elastic ribbon 121 is laid on a surface of the sheet 103b and is bonded therewith. As a result, onto the surface of the sheet 103b, the elastic ribbon 121 is bonded in a desired curved pattern such as a sine curve etc in a plane manner. The components 50 and 60 will be described below.

Unless otherwise specifically noted, in the following description, members for the manufacturing apparatus 40 are each supported at one end by a vertical support wall 100 (a so-called flat panel) through a suitable bracket which is not shown; this support wall 100 extends throughout the total length of the manufacturing apparatus 40 in the MD direction. That is, as shown in FIG. 4B, the support wall 100 stands at the back side in the CD direction (below the plane of the paper in FIG. 4A) along a direction substantially perpendicular to the MD direction (a direction substantially perpendicular to the plane of the paper). The vertical wall of the support wall 100 supports the end section of each member at the back side in the CD direction, but does not support sections the end section at the front side.

(1) Conveying Roller 50

The main body of the conveying roller 50 is a cylinder whose rotational axis C50 is in the horizontal CD direction. The conveying roller 50 rotates at a predetermined peripheral speed V50 in a rotating direction, the rotating direction being along the MD direction. The sheet 103b is fed to the conveying roller 50, for example, from left substantially horizontally. The sheet 103b is wrapped around the outer peripheral face of the conveying roller 50, for example, with a wrapping angle of 180 to 200 degree from a wrapping-start position Ps which is approximately a seven o'clock position in the lower part of the conveying roller 50. The conveying direction of the sheet 103*b* is reversed and the sheet 103*b* is finally sent out (corresponding to "conveying" in Claims) to the left substantially in the horizontal direction at a wrapping-end position Pe which is approximately a twelve o'clock position in the upper part of the conveying roller 50.

It should be noted that, while the sheet 103*b* is being wrapped around the outer peripheral face of the conveying roller 50, the sheet 103*b* and the roller 50 are maintained in a state of substantially no slipping relative to each other. Therefore, the peripheral speed V50 of the conveying roller 50 is substantially the same as the speed V of the sheet 103*b* in the conveying direction (hereinafter referred to as a conveying speed V).

The conveying roller 50 may be configured as a driven roller which is driven and rotated by a power source such as a suitable motor, or as an idler roller which is moved and rotated by the sheet 103*b*. In the latter case, a force to convey the sheet 103*b* is provided by pulling of the sheet 103*b* with another conveying roller etc (not shown), which is located more downstream than the conveying roller 50.

Further, as shown in FIG. 4A, a pressing roll 55 may be disposed opposite to the outer peripheral face of the conveying roller 50; the pressing roll 55 may be pressed against the outer peripheral face of the conveying roller 50 by a predetermined amount of pressure. This can increase bonding strength of the elastic ribbon 121 which is bonded with the sheet 103*b* by the guiding member 60 in a desired curved pattern.

(2) Guiding Member 60

The guiding member 60 includes a plate-like oscillating arm 61 disposed below the conveying roller 50. The oscillating arm 61 has a longitudinal direction and the longitudinal direction thereof is in the horizontal direction. The oscillating arm 61 is arranged extending across the rotational axis C50 of the conveying roller 50 in the horizontal direction. An oscillating end 61*a* thereof, which is located left from the conveying roller 50, can be oscillated in the CD direction about the center which is an axis C61 located right from the conveying roller 50. As an example of a drive mechanism 62 for the oscillating motion, a configuration can be provided which employs the combination of a motor 62*a* that serves as a power source and a crank mechanism 62*b* that transforms the rotation of the drive shaft 62*c* of the motor 62*a* into an oscillating motion of a certain amplitude. However, the configuration is not limited to the one employed in this example, as long as the oscillating motion can be performed. Further, it is also possible to change the rotation speed of the drive shaft 62*c* depending on (in proportion to) the conveying speed V. In this case, the period of the oscillating motion of the oscillating arm 61 is dependent on (in proportion to) the reciprocal of the conveying speed V.

On the oscillating end 61*a*, an oscillating-end roll 63 (corresponding to "drive roller") is supported rotatably about a horizontal rotational axis C63. On the other hand, on a position in the oscillating arm 61 which is located closer to the axis C61 than the oscillating-end roll 63 is, an axis-side roll 64 (corresponding to "second roller") is supported rotatably about a horizontal rotational axis C64.

Therefore, when the elastic ribbon 121 is fed downward along the vertical direction from above at a certain point to the right of the conveying roller 50, the elastic ribbon 121 is wrapped around the outer peripheral face of the axis-side roll 64 firstly and is led to the left of the conveying roller 50. Thereafter, the elastic ribbon 121 comes into contact with the oscillating-end roll 63 located at that position and a direction in which the ribbon 121 proceeds is reversed right by the roller 63. The elastic ribbon 121 is introduced from below the conveying roller 50 in the vicinity of the wrapping-start position Ps of the sheet 103*b*.

During the introducing, the oscillating-end roll 63 moves back and forth in the CD direction in conjunction with the oscillating motion of the oscillating end 61*a*. Therefore, a position in the surface of the sheet 103*b* at which the elastic ribbon 121 is bonded is continuously changing in the CD direction; as a result, the elastic ribbon 121 is bonded in a desired curved pattern with the surface of the sheet 103*b* (corresponding to "bonding" in Claims).

In the introducing, the elastic ribbon 121 is forced substantially flat because the elastic ribbon 121 is wrapped around the outer peripheral face of the axis-side roll 64 and the outer peripheral face of the oscillating-end roll 63. Therefore, the elastic ribbon 121 is bonded with the sheet 103*b* in a plane manner.

Further, in the introducing, the elastic ribbon 121 is in the stretched condition. That is, the elastic ribbon 121 elastically deforms in the transporting direction at a suitable stretching ratio. The elastic ribbon 121 is bonded with the sheet 103*b* in the stretched condition, thereby imparting stretchability to a section of the sheet 103*b* with which the elastic ribbon 121 is bonded. The stretching ratio of the elastic ribbon 121 will be described later.

As shown in FIG. 4B, the oscillating-end roll 63 and the axis-side roll 64 are arranged on a straight line L1, which connects the oscillating end 61*a* of the oscillating arm 61 to the axis C61. Further, the rotational axis C63 of the oscillating-end roll 63 and the rotational axis C64 of the axis-side roll 64 are parallel to each other, and these axes C63 and C64 are fixed to and supported by the oscillating arm 61. Therefore, regardless of the back-and-forth motion of the oscillating-end roll 63 in the CD direction, the outer peripheral face of the axis-side roll 64 constantly faces the oscillating-end roll 63. Therefore, the elastic ribbon 121 can be transported definitely towards the oscillating-end roll 63. This enables the elastic ribbon 121 to move steadily; for example, this can effectively prevent the elastic ribbon 121 from falling out of the oscillating-end roll 63.

However, the invention is not limited to this configuration. For example, it is possible, without fixing the rotational axis C64 of the axis-side roll 64 to the oscillating arm 61, to oscillate the axis C64 independently of the oscillating arm 61 by a suitable actuator such as a motor etc. That is, the configuration may be as follows: the rotational axis C64 of the axis-side roll 64 is supported on the oscillating arm 61 pivotably about an axis perpendicular to the axis C61 and the foregoing actuator is controlled, whereby the rotational axis C64 of the axis-side roll 64 pivots such that the outer peripheral face of the axis-side roll 64 faces the oscillating end 61*a* of the oscillating arm 61 according to the oscillating motion of the oscillating arm 61. This configuration enables the elastic ribbon 121 to move steadily in similarity to the foregoing one.

Also, it is possible, without fixing the rotational axis C63 of the oscillating-end roll 63 to the oscillating arm 61, to support the axis C63 by the oscillating arm 61 pivotably about an axis perpendicular to the axis C61. In this case, the orientation of the outer peripheral face of the oscillating-end roll 63 is determined to balance the difference of the tension in the width direction which is generated within the elastic ribbon 121 wrapped around the roll 63.

Figure 5:
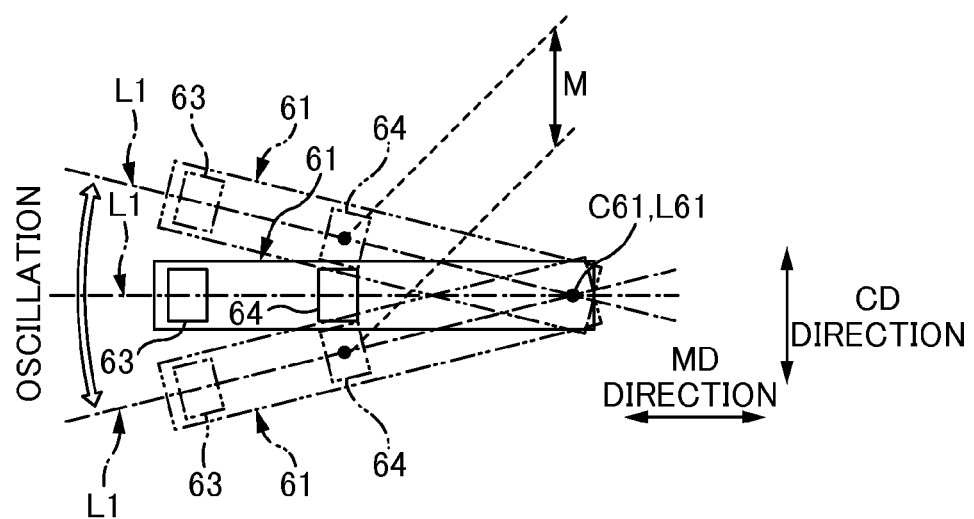
FIG. 5 is an explanatory diagram showing a reason that an axis-side roll 64 of an oscillating arm 61 is preferably arranged in the vicinity of an axis C61.

Further, it is desirable that the axis-side roll 64, whose rotational axis C64 is fixed to and supported by the oscillating arm 61, is arranged as close as possible to the axis C61, as shown in FIG. 4A. This is because, as shown in FIG. 5, as the axis-side roll 64 is positioned farther from the axis C61, the greater the axis-side roll 64 in the CD direction moves in conjunction with oscillating motion of the oscillating arm 61 (the movement M of the roller 64 becomes greater) and the elastic ribbon 121 becomes more likely to slip out of the roller. Therefore, it is most desirable that, as shown in FIGS. 4A and 4B, the axis-side roll 64 is arranged such that the outer peripheral face of the axis-side roll 64 is contact with the rotation centerline L61 of the axis C61. In this embodiment, such configuration is employed.

Further, under the condition that the rotation centerline L61 of the axis C61 is in contact with the outer peripheral face of the axis-side roll 64 as mentioned above, it is desirable that a path R121 in which the elastic ribbon 121 is supplied to the axis-side roll 64 is aligned along the rotation centerline L61 of the axis C61, on the same one line as shown in FIG. 4A. In this case, the torsion of the elastic ribbon 121 caused by the oscillating motion of the oscillating arm 61 appears mainly on a section 121a of the elastic ribbon 121 located upstream from the axis-side roll 64. As a result, the torsion of the elastic ribbon 121 downstream from the axis-side roll 64 is reduced. In this embodiment, such configuration is employed.

<<<Stretching Ratio of Elastic Ribbon 121>>>

As mentioned above, when bonding the elastic ribbon 121 with the sheet 103b, the elastic ribbon 121 is in the stretched condition. That is, the elastic ribbon 121 elastically deforms at a suitable stretching ratio. The stretching ratio means the length L of a member in a stretched condition divided by its original unstretched length L0 (a length under no external force) (=L/L0). The magnitude of the stretching ratio substantially determines the stretchability of the composite sheet, that is, the sheet 103b with which the elastic ribbon 121 has been bonded.

It can be considered that the stretching ratio is the sum of two stretching ratio: one that, in order to transport the elastic ribbon 121 in a tensioned condition, is provided in a process which is performed prior to the manufacturing apparatus 40 according to the present embodiment, and additional one that is provided by the manufacturing apparatus 40. However, the former stretching ratio is omitted below since it is normally smaller than the latter one.

The latter stretching ratio is determined mainly by the ratio (=V/V121) of the conveying speed V of the sheet 103b to the speed V121 of the elastic ribbon 121 (hereinafter referred to as feeding speed V121) at which the ribbon 121 is fed from the preceding process to the guiding member 60 in the transporting direction. That is, the conveying speed V (m/sec) of the sheet 103b is set basically greater than the feeding speed V121 (m/sec) of the elastic ribbon 121. Therefore, with a bonded section of the elastic ribbon 121 with the sheet 103b, the sheet 103b pulls a non-bonded section of the elastic ribbon 121 located upstream from the bonded section in the transporting direction, thereby substantially providing the stretching ratio to the elastic ribbon 121.

The feeding speed V121 can be controlled such that the feeding speed V121 is proportional to the conveying speed V. In this case, the foregoing stretching ratio is maintained constant basically regardless of the conveying speed V. For example, in the case where the conveying speed V is 2V0 and the feeding speed V121 is V0, the stretching ratio is 2 (=2V0/V0). Even if the conveying speed V is 4V0, the stretching ratio is 2 (=4V0/2V0) as long as the feeding speed V121 is set to 2V0; as a result, the magnitude of the stretching ratio is maintained constant.

Figure 6:
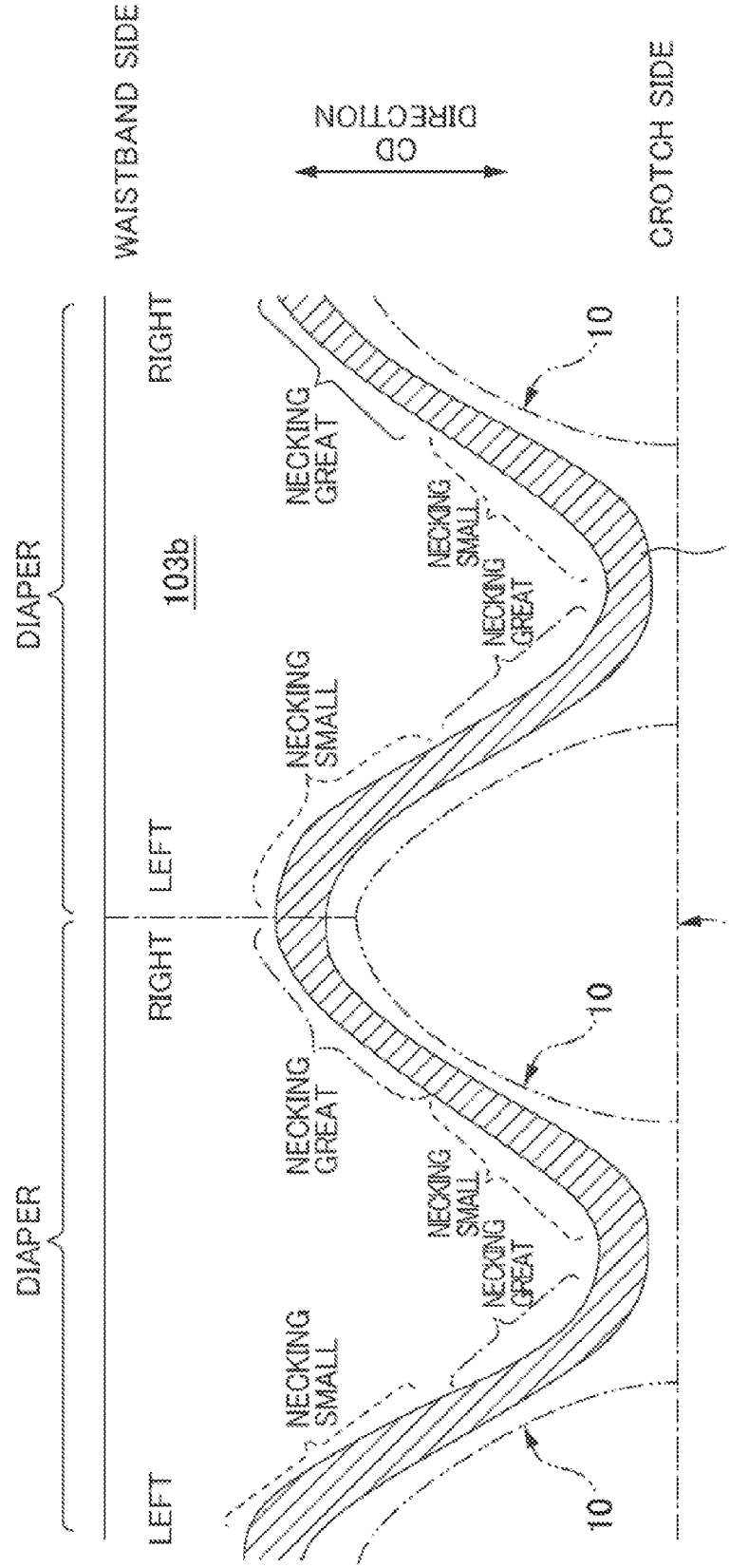
FIG. 6 is an explanatory diagram showing how the degree of necking varies in a curved pattern of an elastic ribbon 121.

However, because in practice the oscillating-end roll 63 moves back and forth in the CD direction, the stretching ratio changes in each section of the curved pattern of the elastic ribbon 121 even if the feeding speed V121 is controlled so as to be proportional to the conveying speed V as mentioned above (in other words, such that the ratio of the feeding speed V121 to the conveying speed V is constant). FIG. 6 is an explanatory diagram thereof; more specifically, it is a plan view of the composite sheet, that is, the sheet 103b with which the elastic ribbon 121 has been bond.

With reference to FIG. 6, it can be understood that the width of the elastic ribbon 121 is not uniform, that is, necking (shrinkage in width) occurs in each section of the curved pattern. In addition, the degree of necking varies. In a section where the degree of necking is great, a larger stretching ratio is provided than sections surrounding that section.

Herein, one of the most serious problems is that the stretching ratio becomes asymmetric with respect to the right and the left of the diaper 1 when a final product of the diaper 1 is taken from the composite sheet. This leads to the asymmetrical stretchability of the diaper 1 in the left and the right sides thereof; therefore the diaper 1 becomes uncomfortable to wear.

With this point in mind, referring to FIG. 6 will reveal that the stretching ratio is asymmetric in the example of the figure also. For example, comparing the sections indicated by the dotted lines in FIG. 6 to the sections indicated by the dot dash lines, the degree of necking is different from each other. Specifically speaking, in the waistband (waist) side of the diaper 1, the necking on the right side is greater than on the left side, and, that is, the stretching ratio on the right side is high than on the left side. On the contrary, in the crotch side of the diaper 1, necking on the right side is smaller than on the left side, and, that is, the stretching ratio on the right side is low than on the left side. Therefore, in order for the stretching ratio to be symmetric, it is necessary to adjust the stretching ratio of the elastic ribbon 121 in the curved pattern.

Further, there are needs for setting the stretching ratio which is different from each section of the curved pattern according to a type of the diaper 1. For example, there is a demand for reducing the stretchability in the crotch section 1b in order to prevent the absorbent body 4 from creasing, as mentioned above with reference to FIG. 3. In this case, it is necessary to adjust the stretching ratio of the elastic ribbon 121 in each section of the curved pattern.

In the present embodiment, the oscillating-end roll 63 can be driven and rotated. Also, the rotation speed V63 of the oscillating-end roll 63 changes in the process of introducing the elastic ribbon 121 into the sheet 103b, thereby adjusting the stretching ratio in the curved pattern.

Figure 7A:
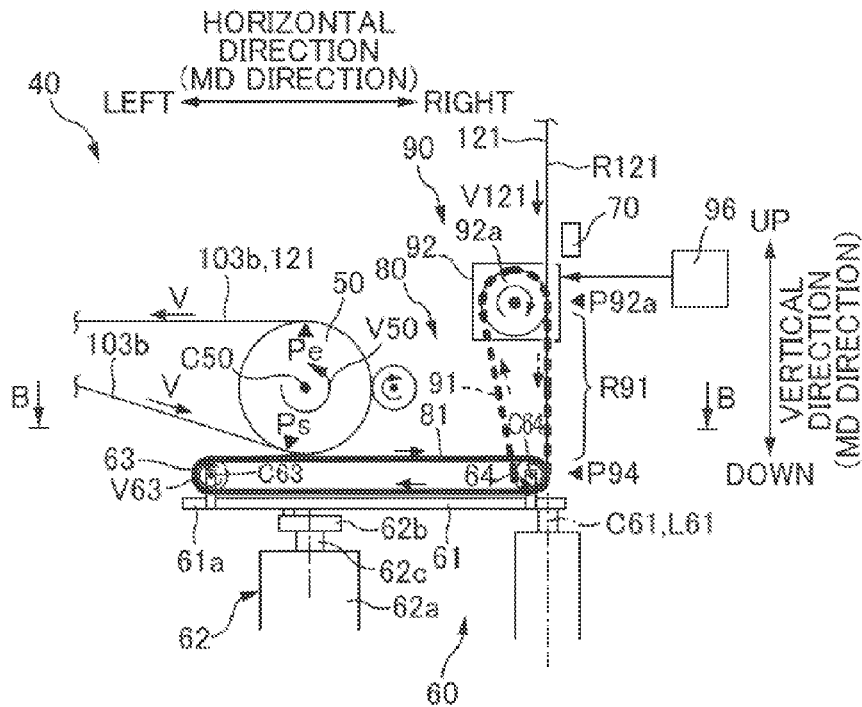
FIG. 7A is a side view showing a drive mechanism 80 which drives and rotates an oscillating-end roll 63.
Figure 7B:
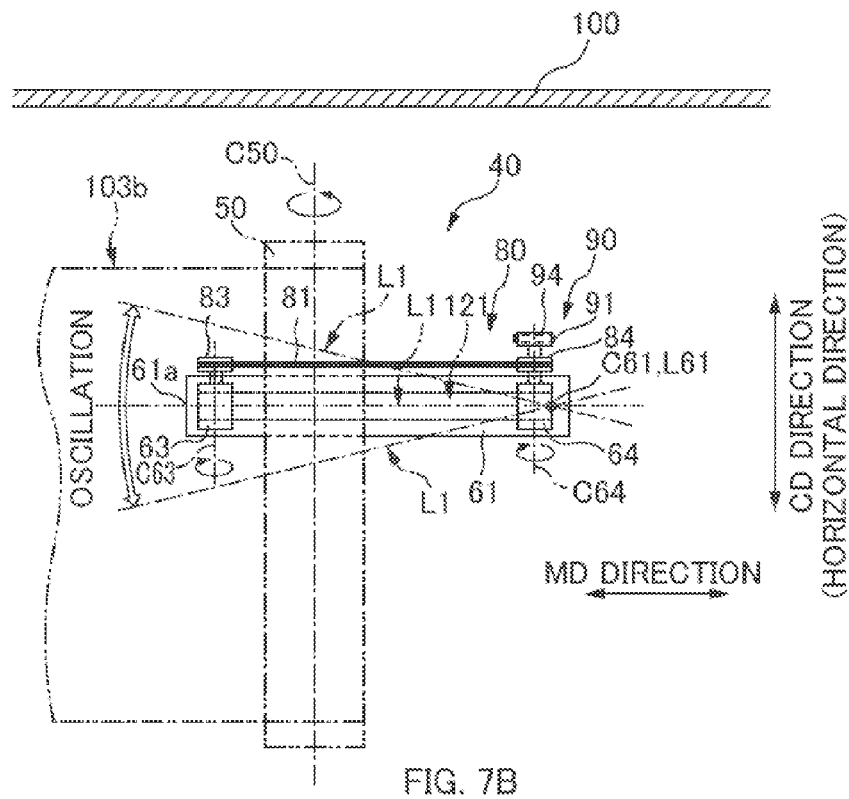
FIG. 7B is a view taken along line B-B in FIG. 7A.

FIGS. 7A and 7B are explanatory diagrams of a drive mechanism 80 which drives and rotates the oscillating-end roll 63. FIG. 7A is a side view of the manufacturing apparatus 40, and FIG. 7B is a view taken along line B-B in FIG. 7A.

The drive mechanism 80 is a so-called endless belt power transmission device having endless belts 81 and 91. The drive mechanism 80 includes: an oscillating-end pulley 83 (corresponding to "drive pulley"); a relay pulley 84; an endless belt 81; and a second drive mechanism 90. The oscillating-end pulley 83 is disposed such that it rotates so as to rotate about the same axis as the oscillating-end roll 63 in an integrated manner with the oscillating-end roll 63. The relay pulley 84 is arranged on the oscillating arm 61 at a position closer to the axis C61 than the oscillating-end pulley 83 is. The endless belt 81 is wrapped around the oscillating-end pulley 83 and the relay pulley 84. The second drive mechanism 90 drives and rotates the relay pulley 84. The second drive mechanism 90 includes: a motor 92 which functions as a power source; a second relay pulley 94 which is disposed so as to rotate about the same axis as the relay pulley 84 in an integrated manner with the relay pulley 84; a second endless belt 91 which is wrapped around a drive shaft 92*a* of the motor 92 and the second relay pulley 94, and a controller 96 such as a computer, a sequencer which controls the motor 92. The driving torque of the drive shaft 92*a* of the motor 92 is transmitted finally to the oscillating-end roll 63, through the members in the following order: the second endless belt 91, the second relay pulley 94, the relay pulley 84, endless belt 81, and the oscillating-end pulley 83. As a result, the oscillating-end roll 63 is driven and rotated.

In this example, the controller 96, for example, controls the rotation speed V63 to increase or decrease it based on a reference velocity (hereinafter referred to as a basis speed) having a predetermined value. As an example of the predetermined value, there is provided the foregoing feeding speed V121, that is, the feeding speed V121 at which the elastic ribbon 121 is fed from the preceding process to the guiding member 60. In this case, even if the stretching ratio changes in each section of the curved pattern due to the back-and-forth motion in the CD direction, the stretching ratio averaged over one period of the curved pattern is as follows: the elastic ribbon 121 is stretched, as a whole, at the stretching ratio based on the ratio of the conveying speed V to the feeding speed V121 which is the basis speed (=V/V121) (hereinafter referred to as an average stretching ratio).

Therefore, when, for a part of the elastic ribbon 121, the oscillating-end roll 63 rotates at the basis speed, the average stretching ratio is provided to the part. On the other hand, when the oscillating-end roll 63 rotates faster than the basis speed, the stretching ratio lower than the average stretching ratio is provided to the part. When the roll 63 rotates slower than the basis speed, the stretching ratio higher than the average stretching ratio is provided to the part. That is, by changing the rotation speed V63 of the oscillating-end roll 63, the stretching ratio can change in each section of the curved pattern. As mentioned above, when the feeding speed V121 changes in proportion to the conveying speed V, the basis speed, which is the feeding speed V121, changes in proportion to the conveying speed V. Therefore, the rotation speed V63 changes in proportion thereto.

If the stretching ratio can be adjusted in such a manner, the asymmetric problem of the stretching ratio can be solved. In addition, it is possible to satisfy the foregoing needs to provide the stretching ratio to each section of the curved pattern.

For example, the asymmetric problem can be solved as follows: the trend in irregularity of the necking in the curved pattern is examined in advance, and the rotation speed V63 of the oscillating-end roll 63 changes depending on the trend such that such irregularity is eliminated.

As can be seen in FIG. 6, the irregularity trend of the necking does not depends on whether the forward path or the backward path in the back-and-forth motion in the CD direction. That is, the necking after passing a turning point of the back-and-forth motion (ranges indicated by the dot dash lines in FIG. 6) tends to be larger than the necking prior to the passing (ranges indicated by the dotted lines in FIG. 6). Therefore, within a time period including the a turning point for the back-and-forth motion, the rotation speed V63 of the oscillating-end roll 63 is less than the basis speed prior to the turning point. On the other hand, after the turning point, the rotation speed V63 is greater than the basis speed. This can eliminate the irregularity of the necking.

Further, because the needs obviously can be satisfied, a description thereof is omitted.

For both of the foregoing problem or needs, it is basically necessary to adjust the stretching ratio corresponding to the forming operation of the curved pattern. In the present embodiment, the curved pattern is formed by moving back and forth of the oscillating-end roll 63 in the CD direction. And, the stretching ratio is adjusted by changing the rotation speed V63 of the oscillating-end roll 63. That is, the oscillating-end roll 63 performs concurrently both of forming the curved pattern of the elastic ribbon 121 and adjusting the stretching ratio of the elastic ribbon 121. This makes it easier to provide each section of the curved pattern with a desired stretching ratio corresponding to the section.

FIGS. 8A and 8B are explanatory diagrams of a specific example of the corresponding. FIG. 8A is a timing chart of oscillating motion of the oscillating arm 61, that is, back-and-forth motion of the oscillating-end roll 63. FIG. 8B is a timing chart of the rotation speed V63 of the oscillating-end roll 63. In both figures, the horizontal axes are time.

The back-and-forth motion of the oscillating-end roll 63 is generated by transforming the rotation of the motor 62*a* of the drive mechanism 62 into the oscillating motion of the oscillating arm 61 with the crank mechanism 62*b*, as mentioned above. That is, the back-and-forth motion is performed with the period in which the drive shaft 62*c* of the motor 62*a* rotates one time. Therefore, as shown in FIG. 8A, the elastic ribbon 121 forms a curved pattern, which is substantially a sine curve. Further, the oscillating-end roll 63 is rotated by the motor 92 of the drive mechanism 80. Herein, assume that the controller 96 of the motor 92 is configured such that the rotation speed of the drive shaft 92*a* of the motor 92 is changed based on a desired change pattern and the change pattern changes with a period in which the drive shaft 62*c* of the motor 62*a* for the back-and-forth motion rotates one time. In this case, as shown in FIG. 8B, the speed pattern of the rotation speed V63 of the oscillating-end roll 63 has the same period as the curved pattern in FIG. 8A. Therefore, just by matching the phases of the rotation of the drive shaft 62*c* of the motor 62*a* and the rotation of the drive shaft 92*a* of the motor 92, a desired stretching ratio corresponding to each section of the curved pattern can be provided to the section. This makes it easier to provide the desired corresponding stretching ratio to each section of the curved pattern.

In this regard, it is desirable that the speed pattern of the rotation speed V63 of the oscillating-end roll 63 is delayed by a predetermined phase from the back-and-forth motion of the oscillating-end roll 63. In this case, to each section of the elastic ribbon 121 on the curved pattern, a desired stretching ratio precisely corresponding thereto can be provided. The reason is as follows: the elastic ribbon 121 moves back and forth with a slight delay from the back-and-forth motion of the oscillating-end roll 63, the ribbon 121 is bonded with the sheet 103*b*, and thereby the change of the rotation speed V63 of the oscillating-end roll 63 is transmitted relatively instantly to the bonding position of the sheet 103*b* and the elastic ribbon 121.

Further, the oscillating-end roll 63 functions as a device for forming the curved pattern and the device for providing the stretching ratio. Therefore, the length of the path D between the device for forming the curved pattern and the device for providing the stretching ratio is zero (see FIG. 1 for the path D). This can prevent the stretching ratio from being smoothed out on the course of the path D. As a result, it is easier to set a practically different stretching ratio to each section in the curved pattern.

Incidentally, in the example shown in FIGS. 7A and 7B, the axis-side roll 64 is driven and rotated. That is, the relay pulley 84 disposed closer to the axis C61 is fixed so as to rotate about the same axis as the axis-side roll 64 in an integrated manner with the axis-side roll 64. Therefore, the axis-side roll 64 is connected to the oscillating-end roll 63 through the endless belt 81, and is driven and rotated in conjunction with the oscillating-end roll 63 at the same peripheral speed as the roll 63.

In this configuration, when changing the peripheral speed, which is the rotation speed V63 of the oscillating-end roll 63, to the elastic ribbon 121, the peripheral speed V64 of the axis-side roll 64 is also changed in synchronization therewith. Therefore, the transportation of the elastic ribbon 121 in the transporting direction is controlled by at least these two rollers 63 and 64. This can effectively prevent the oscillating-end roll 63 from slipping relative to the elastic ribbon 121 when changing the peripheral speed V63 of the oscillating-end roll 63. As a result, the change of the stretching ratio can respond better to the change of the rotation speed V63, that is, the peripheral speed.

However, if there is little problem with the response of the change of the stretching ratio, it is not necessary to drive and rotate the axis-side roll 64. The axis-side roll 64 may be an idler roller. That is, the axis-side roll 64 may be an idler roller which is in contact with the elastic ribbon 121 and thereby is moved and rotated by obtaining force to rotate from the elastic ribbon 121. In this case, the relay pulley 84 and the axis-side roll 64 are separated so as to rotate about the rotational axis C64 independently.

Further, in view of improvement of the response of the change of the foregoing stretching ratio, it is preferable that the elastic ribbon 121 is wrapped around the outer peripheral face of the oscillating-end roll 63 at a wrap angle of 90 degree or more and less than 270 degree; in the example of FIG. 4A, approximately 170 degree. Setting the wrap angle can increase the friction between the oscillating-end roll 63 and the elastic ribbon 121. Therefore, due to the friction, the rotation of the oscillating-end roll 63 can be transmitted to the elastic ribbon 121 definitely. As a result, the changing of the rotation speed V63 of the oscillating-end roll 63 enables the stretching ratio of the elastic ribbon 121 to change with high response rate.

Figure 9:
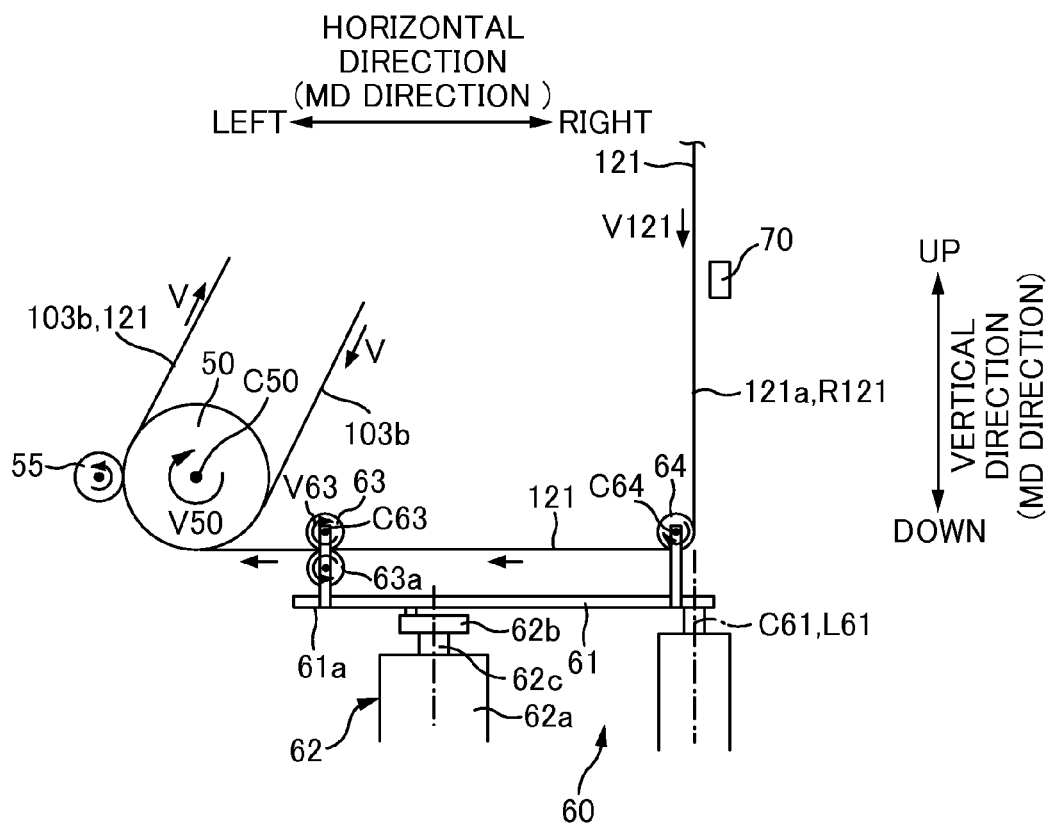
FIG. 9 is a diagram of an example in which it is difficult to insure the wrap angle of the elastic ribbon 121 on the oscillating-end roll 63.

As represented by the example of FIG. 9, if it is difficult to ensure the wrap angle having the foregoing range due to the lay out of the members such as the conveying roller 50 etc, a pressing roll 63a may be disposed opposite to the outer peripheral face of the oscillating-end roll 63 and the pressing roll 63a may be pressed against the outer peripheral face by a predetermined amount of pressure. In this case, because the elastic ribbon 121 is sandwiched and held between the oscillating-end roll 63 and the pressing roll 63a, it is possible to keep high friction between the elastic ribbon 121 and the rolls. Thereby the same effect as the case of wrapping the elastic ribbon 121 around the outer peripheral face of the oscillating-end roll 63 can be achieved. It should be noted that, as long as the pressing roll 63a rotates at substantially the same peripheral speed as the oscillating-end roll 63, the pressing roll 63a may be an idler roller which is moved and rotated, or may be a drive roller which is driven and rotated by a predetermined power source.

Further, with reference to FIG. 4A, in the present embodiment, the oscillating-end roll 63 is one of the members of the manufacturing apparatus 40 which can come into contact with a section of the elastic ribbon 121 to be bonded with the sheet 103b, and among such members, is located the farthest downstream in the transporting direction. Therefore, the stretching ratio adjusted by changing the rotation speed V63 of the oscillating-end roll 63 is not disturbed by other members. This makes it possible to change the stretching ratio of the elastic ribbon 121 definitely based on the rotation speed V63 of the oscillating-end roll 63.

Figure 10:
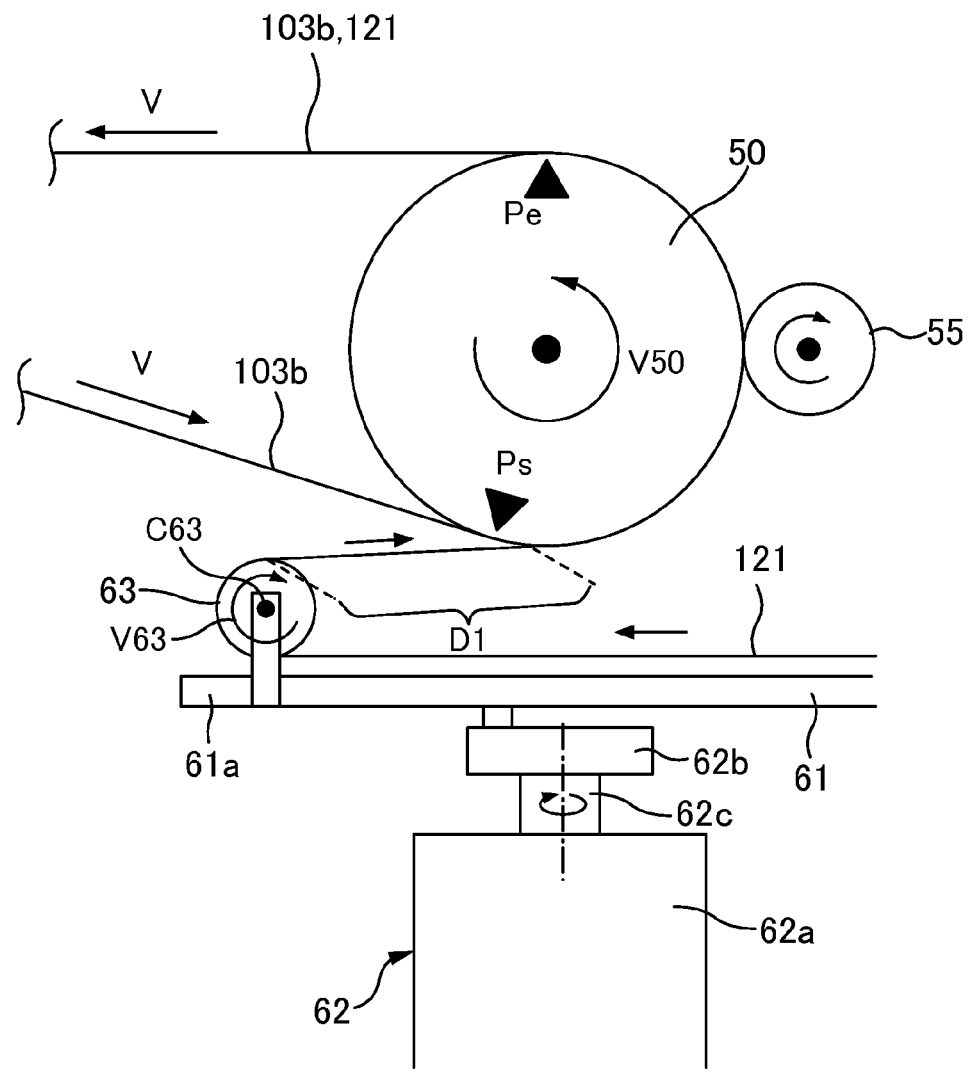
FIG. 10 is a magnified view of the oscillating-end roll 63 and a conveying roller 50 and the vicinity thereof.

Further, as shown in the magnified view of FIG. 10, in the present embodiment, the path length D1 of the elastic ribbon 121 from leaving the outer peripheral face of the oscillating-end roll 63 up to bonding with the sheet 103b is within 30 to 80 mm. This can reduce the degree of smoothing of the stretching ratio in the path length D1. As a result, it is easier to set a practically different stretching ratio to each section in the curved pattern.

Incidentally, in this embodiment, the motor 92 of the second drive mechanism 90 shown in FIG. 7A is fixed to the foregoing support wall 100 (flat panel) and is supported by a supporting member such as bracket etc which is not shown. Therefore, the motor 92 does not oscillate together with the oscillating arm 61. On the other hand, the second relay pulley 94, to which driving torque is input from the motor 92 through the second endless belt 91, is disposed in an integrated manner with the axis-side roll 64. Therefore, the second relay pulley 94 oscillates with the oscillating arm 61 in the CD direction. Thus, the second endless belt 91, which extends between the drive shaft 92a of the motor 92 and the second relay pulley 94, undergoes deformation such as torsion etc according to the oscillating motion of the oscillating arm 61. If the amount of the deformation is great, it is possible that fatigue damage etc of the second endless belt 91 becomes more likely to happen and the life thereof becomes shorter.

In order to reduce the deformation amount of the second endless belt 91 caused by the oscillating motion, in the present embodiment, the drive shaft 92a of the motor 92 is arranged in the vicinity of the rotation centerline L61 of the axis 61 in the same manner as the second relay pulley 94. Therefore, in a path of the second endless belt 91, the section R91 from the drive shaft 92a of the motor 92 to the second relay pulley 94 is parallel to the rotation centerline L61 of the axis C61. In other words, the second endless belt 91 is parallel to the rotation centerline L61 of the axis C61 in the section R91 from the wrapping-end position P92a of the second endless belt 91 on the drive shaft 92a to the wrapping-start position P94 on the second relay pulley 94. This configuration can effectively prevent from torsion of the second endless belt 91 which can be caused by the oscillating motion of the oscillating arm 61.

It should be noted that, in order to prevent completely the foregoing torsion deformation of the second endless belt 91, it is sufficient that the motor 92 is installed on the oscillating arm 61 and is oscillated together with the oscillating arm 61. That is, it is sufficient that the motor 92 is supported by and fixed to the oscillating arm 61 through a suitable bracket. However, in this configuration, the moment of inertia related to the oscillating motion of the oscillating arm 61 increases according to the inertia mass of the motor 92. Therefore, in this regard, the configuration in which the foregoing motor 92 is supported by the support wall 100 is superior.

Other Embodiments

Embodiments of the present invention have been described as above, however the present invention is not limited to these embodiments and the following variations are also possible.

In the foregoing embodiment, an endless belt power transmission device is employed as the drive mechanism 80 which drives and rotates the oscillating-end roll 63 and the axis-side roll 64. However, the drive mechanism is not limited thereto. For example, a configuration with a so-called direct drive can be applied. That is, the oscillating-end roll 63 or the axis-side roll 64 may be driven and rotated by connecting a drive shaft of a power source such as a motor directly to the rollers 63 and 64 co-axially, using a suitable coupling. In this case, the power source such as a motor is provided for each of the rollers 63 and 64 to be driven and rotated. These power sources are installed on and fixed to the oscillating arm 61, for example. In this configuration, the influence of action delay caused by an intermediate member such as the endless belts 81 and 91 can be practically eliminated, thereby improving the response of the members to control. However, the inertia mass of the power source installed on the oscillating arm 61 increases the moment of inertia relative to the oscillating motion of the oscillating arm 61. Therefore, in this regard, the endless belt power transmission device is better.

In the foregoing embodiment, the configuration is provided in which at least the oscillating-end roll 63 is driven and rotated. However, the invention is not limited thereto. The oscillating-end roll 63 may be an idler roller which is moved and rotated. That is, it is possible that only the axis-side roll 64 is driven and rotated. In this case, the length of a path becomes longer between the axis-side roll 64 which functions to provide the stretching ratio and the bonding position of the elastic ribbon 121 with the sheet 103*b*. Therefore, even if the stretching ratio is changed by the rotation speed V64 of the axis-side roll 64, the stretching ratio is more likely to be smoothed out in the path length. As a result, this configuration is inferior to the configuration in which only the oscillating-end roll 63 is driven and rotated or the configuration in which both the oscillating-end roll 63 and the axis-side roll 64 are driven and rotated.

In the foregoing embodiment, the configuration is provided in which the oscillating arm 61 includes two rollers, the oscillating-end roll 63 and the axis-side roll 64. However, the invention is not limited thereto. One or more additional rollers may be disposed between the oscillating-end roll 63 and the axis-side roll 64. In this case, the rotational axes of those additional rollers are preferably parallel to the rotational axes C63 and C64 of the oscillating-end roll 63 and the axis-side roll 64. Further, the additional roller may be an idler roller, but may be a roller which is driven and rotated. In the case of a driven roller, for example, the additional roller is provided with a pulley so as to rotate about the same axis as the pulley in an integrated manner with the pulley, and the endless belt 81 is wrapped around that pulley. Thereby, a necessary driving torque to drive and rotate the roller is provided by the endless belt 81.

Figure 11A:
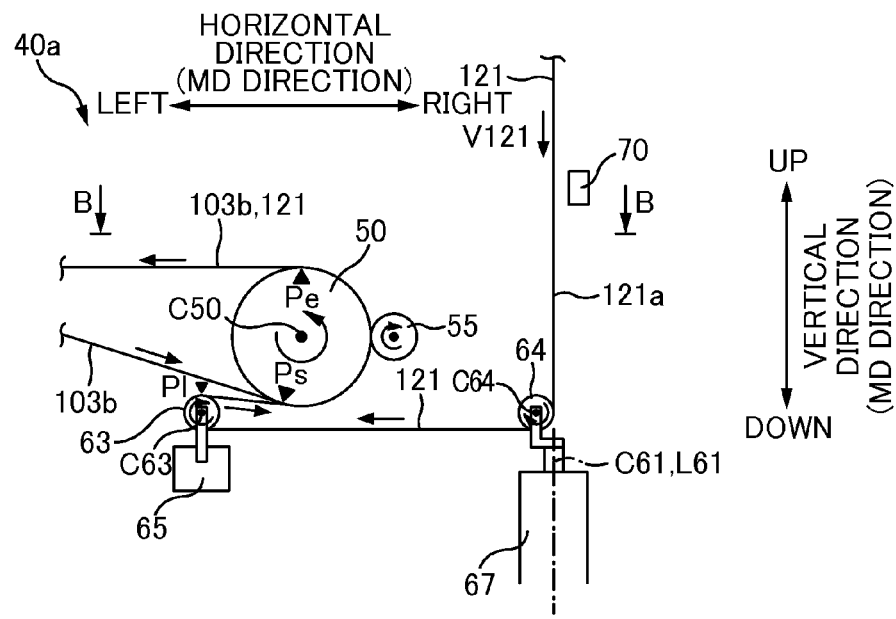
FIG. 11A is a side view of a manufacturing apparatus for a composite sheet 40a according to the other embodiments.
Figure 11B:
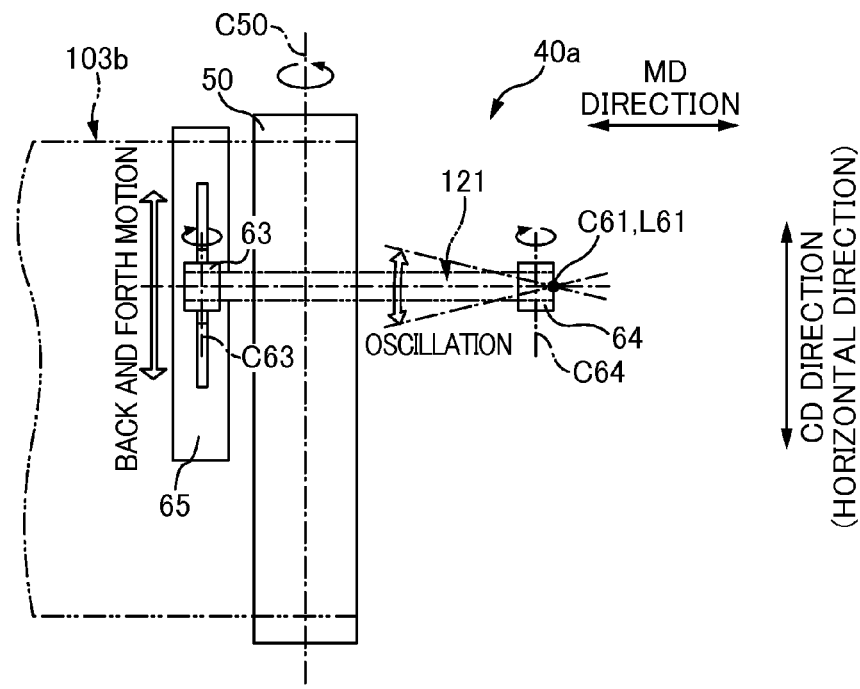
FIG. 11B is a view taken along line B-B in FIG. 11A.

In the foregoing embodiment, the configuration is provided in which the oscillating arm 61 is provided with the oscillating-end roll 63 and the axis-side roll 64. However, the oscillating arm 61 may be omitted. That is, as shown in FIGS. 11A and 11B, a configuration may be employed which includes: a guiding member 65 such as a linear rail that guides the oscillating-end roll 63 in the CD direction such that the roll 63 can move back and forth; a drive mechanism (not shown) such as motor etc that moves back and forth the oscillating-end roll 63 in the CD direction; a supporting member 67 that supports the rotational axis C64 of the axis-side roll 64 such that the axis C64 can oscillate pivotably about the axis C61; a drive mechanism (not shown) that oscillates the axis-side roll 64; and a controller (not shown) such as a computer etc which controls the drive mechanism such that the outer peripheral face of the axis-side roll 64 faces the oscillating-end roll 63 according to (in synchronization with) the back-and-forth motion of the oscillating-end roll 63. In this case, as a matter of course, the oscillating-end roll 63 and the axis-side roll 64 are driven and rotated by the drive mechanism 80 such as an endless belt power transmission device etc in the same way as the embodiment shown in FIGS. 7A and 7B, though it is not shown in the figure.

In the foregoing embodiment, the elastic ribbon 121 is provided as an example of the continuous body of the elastic member. However, the invention is not limited thereto. A elastic thread member such as rubber thread etc may be employed.

In the foregoing embodiment, sine curve is provided as an example of the curved pattern of the elastic ribbon 121. However, the invention is not limited thereto. The curved pattern may be a curved line other than sine curve. Obviously, sine curve is just a desired target shape, and, in practice, a curved pattern of the elastic ribbon 121 which is formed after bonding with the sheet 103*b* may be slightly different from the target shape.

In the foregoing embodiment, the shapes of the oscillating-end roll 63 and the axis-side roll 64 are not described in detail. As these rollers 63 and 64, a flat roll whose outer peripheral face is flat across the width direction of the roller (CD direction) may be employed, and also a crown-roller may be used. The crown-roller means a roller whose section having the maximum diameter is the center of the roller in the width direction. In a case of using this roller, due to the maximum diameter section of the outer peripheral face, a force towards the center of the roller in the width direction is provided to the elastic ribbon 121 which is wrapped around the outer peripheral face thereof. Thereby, the elastic ribbon 121 is less likely to slip out of the roller. As an example of such crown-roller, there are provided a roller having an annular rib which is formed along the circumferential direction only on the center of the outer peripheral face, a roller having a diameter which increases gradually from the both ends of the outer peripheral face towards the center thereof, or the like.

In the foregoing embodiment, as shown in FIG. 2A, the rotation centerline L61 of the axis C61 is aligned along the up-and-down direction (vertical direction), the rotational axis C50 of the conveying roller 50 is aligned along the CD direction (horizontal direction). However, the invention is not limited thereto as long as these are perpendicular to each other. That is, it is sufficient that the rotation centerline L61 of the axis C61 is perpendicular to the rotational axis C50 of the conveying roller 50.

In the foregoing embodiment, the rotational axis C63 of the oscillating-end roll 63 and the rotational axis C64 of the axis-side roll 64 are aligned along the horizontal direction. The reason is that the elastic ribbon 121 becomes in a flat shape without torsion when the elastic ribbon 121 is transferred to the conveying roller 50 whose the rotational axis C50 is in the horizontal direction, that is, the CD direction. Therefore, the orientation of the rotational axes C63 and C64 of the oscillating-end roll 63 and the axis-side roll 64 is not limited to the horizontal direction. The orientation of these axes can change according to the orientation of the rotational axis C50 of the conveying roller 50. That is, it is sufficient that the rotational axis C63 of the oscillating-end roll 63 and the rotational axis C64 of the axis-side roll 64 are arranged such that the plane defined by these rotational axes C63 and C64 in the oscillating motion of the oscillating arm 61 is parallel to the rotational axis C50 of the conveying roller 50. Furthermore, it is sufficient that the oscillating-end roll 63 and the axis-side roll 64 are arranged such that the rotational axes C63 and C64 are perpendicular to the axis C61 which is perpendicular to the rotational axis C50 of the conveying roller 50.

In the foregoing embodiment, hot melt adhesive is applied to the elastic ribbon 121 by the applying device 70. However, the invention is not limited thereto as long as the sheet 103b and the elastic ribbon 121 can bond together. For example, hot melt adhesive may be applied to the sheet 103b, or may be applied to both the elastic ribbon 121 and the sheet 103b. Further, instead of the adhesion, hot-melt bonding by embossing etc may be employed.

In the foregoing embodiment, the outer sheet 3b of the back face sheet 3 of the diaper 1 is manufactured using a manufacturing method for a composite sheet according to the invention. However, the invention is not limited thereto. For example, a solid gather sheet which forms solid gather of the diaper 1 may be manufactured. In this case, a section in the surface of the sheet 103b on which the elastic ribbon 121 bonds with the sheet 103 stands due to shrinkage of the elastic ribbon 121 forms solid gather.

In the foregoing embodiment, a manufacturing method for a composite sheet according to the invention is applied to manufacturing of the pull-on diaper 1. However, the invention is not limited thereto. Also, the method may be applied to manufacturing of a wrap-style diaper (a diaper which is worn by fastening the front waistband section 1a and the back waistband section 1c thereof with a fastening tape).

REFERENCE SIGNS LIST 1 disposable diaper (absorbent article),
1a front waistband section, 1b crotch section, 1c back waistband section,
2 surface sheet, 3 back face sheet, 3a inner sheet, 3b outer sheet,
4 absorbent body, 10 leg opening section, 11 longitudinal end flap,
12 side end flap, 16 waist elastic member,
21 front elastic ribbon, 22 back elastic ribbon,
40 manufacturing apparatus for composite sheet, 40a manufacturing apparatus for composite sheet,
50 conveying roller (conveying mechanism), 55 pressing roll,
60 guiding member, 61 oscillating arm, 61a oscillating end,
61 drive mechanism, 62a motor, 62b crank mechanism, 62c drive shaft,
63 oscillating-end roll (drive roller), 63a pressing roll,
64 axis-side roll (second roller), 65 guiding member, 67 supporting member,
70 applying device, 80 drive mechanism, 81 endless belt,
83 oscillating-end pulley (drive pulley), 84 relay pulley,
90 second drive mechanism, 91 endless belt, 92 motor, 92a drive shaft,
94 second relay pulley, 96 controller,
100 support wall, 103b sheet (continuous body of sheet),
121 elastic ribbon (continuous body of elastic member), 121a section,
L1 straight line, Ps wrapping-start position, Pe wrapping-end position,
C50 rotational axis, C61 axis, L61 rotation centerline,
C63 rotational axis, C64 rotational axis,
P92a wrapping-end position, P94 wrapping-start position, R91 section,

The invention claimed is:

1. A manufacturing apparatus for a composite sheet associated with an absorbent article, in which a continuous body of an elastic member is in a stretched state and is bonded with a continuous body of a sheet, said manufacturing apparatus comprising:
a controller;
a conveying mechanism configured to continuously convey the continuous body of the sheet in a conveying direction; and
a guiding member configured to
transport the continuous body of the elastic member in a transporting direction towards the continuous body of the sheet while moving, in a back-and-forth motion, the continuous body of the elastic member in an intersecting direction that intersects the conveying direction, the continuous body of the sheet being traveling in the conveying direction, and
bond the continuous body of the elastic member with the continuous body of the sheet while a position on the continuous body of the sheet at which the continuous body of the elastic member bonds with the continuous body of the sheet is continuously changing in the intersecting direction by the back-and-forth motion,
wherein
the guiding member includes
a drive roller configured to be driven and rotated along the transporting direction while being contact with the continuous body of the elastic member,
an oscillating arm configured to oscillate about a predetermined axis in the intersecting direction, wherein the drive roller is disposed on an oscillating end of the oscillating arm,
a second roller disposed on the oscillating arm at a position closer to the predetermined axis than the drive roller and configured to be driven and rotated at a same rotation speed as the drive roller to transport the continuous body of the elastic member to the drive roller, and
the controller is configured to change the rotation speed of the drive roller to adjust a stretching ratio of the continuous body of the elastic member.

2. The manufacturing apparatus according to claim 1, wherein, among members that come into contact with the continuous body of the elastic member on a path prior to the bonding of the continuous body of the elastic member with the continuous body of the sheet, the drive roller is located farthest downstream in the transporting direction.

3. The manufacturing apparatus according to claim 2, wherein the conveying mechanism and the drive roller are configured such that a length of a path of the continuous body of the elastic member between a rotational axis of the drive roller up to the bonding with the continuous body of the sheet is from 30 to 80 mm.

4. The manufacturing apparatus according to claim 2, further comprising:
a drive mechanism configured to drive and rotate the drive roller,
wherein the drive mechanism includes
a drive pulley disposed so as to rotate about a same rotational axis as the drive roller in an integrated manner with the drive roller,
a relay pulley arranged on the oscillating arm at a position closer to the predetermined axis than the drive pulley, an endless belt wrapped around the drive pulley and the relay pulley, and a second drive mechanism configured to drive and rotate the relay pulley.

5. The manufacturing apparatus according to claim 4, wherein the second roller is coaxially fixed to the relay pulley to rotate in an integrated manner with the relay pulley, the relay pulley is configured to transmit a driving torque of the second drive mechanism to the second roller through the endless belt to drive and rotate the second roller, and the second drive mechanism is configured to generate the driving torque to rotate the second roller at a same rotational speed as the drive roller.

6. The manufacturing apparatus according to claim 4, wherein the second drive mechanism includes
a drive shaft configured to be driven and rotated,
a second relay pulley coaxially disposed with the relay pulley and configured to rotate in an integrated manner with the relay pulley, and
a second endless belt wrapped around the drive shaft and the second relay pulley, and in a path of the second endless belt, a section from the drive shaft to the second relay pulley is parallel to a rotation centerline of the predetermined axis.

7. The manufacturing apparatus according to claim 1, wherein an outer peripheral face of the drive roller is configured to be wrapped around by the continuous body of the elastic member with a wrap angle of 90 degree or more.

8. The manufacturing apparatus according to claim 1, wherein the guiding member further comprises a rotatable pressing roll opposite to an outer peripheral face of the drive roller, and the pressing roll is configured to press the continuous body of the elastic member against and into contact with the outer peripheral face of the drive roller.

9. The manufacturing apparatus according to claim 1, wherein the controller is configured to change the rotation speed of the drive roller in conjunction with the back-and-forth motion of the guiding member.

10. The manufacturing apparatus according to claim 1, wherein within a time period including a turning point in the back-and-forth motion, prior to passing the turning point, the controller is configured to have the rotation speed less than a predetermined reference velocity, and after passing the turning point, the controller is configured to have the rotation speed greater than the reference velocity.

11. The manufacturing apparatus according to claim 1, wherein the controller is configured to change the rotation speed periodically based on a predetermined speed pattern of the drive roller, and a period of a back-and-forth motion of the guiding member is the same as a period of the speed pattern and the speed pattern is delayed by a predetermined phase from the back-and-forth motion.

* * * * *